US011122974B2

(12) United States Patent
Tokuda et al.

(10) Patent No.: US 11,122,974 B2
(45) Date of Patent: Sep. 21, 2021

(54) OPHTHALMOLOGIC INFORMATION PROCESSING APPARATUS, OPHTHALMOLOGIC SYSTEM, OPHTHALMOLOGIC INFORMATION PROCESSING METHOD, AND RECORDING MEDIUM

(71) Applicant: TOPCON CORPORATION, Tokyo (JP)

(72) Inventors: Kanichi Tokuda, Saitama (JP); Tsutomu Kikawa, Adachi-ku (JP); Hiroyuki Ueda, Adachi-ku (JP)

(73) Assignee: TOPCON CORPORATION, Tokyo (JP)

( * ) Notice: Subject to any disclaimer, the term of this patent is extended or adjusted under 35 U.S.C. 154(b) by 217 days.

(21) Appl. No.: 16/525,598

(22) Filed: Jul. 30, 2019

(65) Prior Publication Data

US 2020/0093369 A1 Mar. 26, 2020

(30) Foreign Application Priority Data

Sep. 25, 2018 (JP) .............................. JP2018-179180

(51) Int. Cl.
*G06K 9/00* (2006.01)
*G01C 3/08* (2006.01)
(Continued)

(52) U.S. Cl.
CPC .......... *A61B 3/1225* (2013.01); *A61B 3/0041* (2013.01); *A61B 3/102* (2013.01);
(Continued)

(58) Field of Classification Search
USPC ................. 382/100, 106–107, 115, 117–118, 382/128–133, 168, 173, 181, 199, 209,
(Continued)

(56) References Cited

U.S. PATENT DOCUMENTS

2012/0194783 A1  8/2012  Wei et al.
2013/0039557 A1  2/2013  Wei et al.
(Continued)

FOREIGN PATENT DOCUMENTS

EP    3 054 420 A2    8/2016
JP    2014-505552 A   3/2014
(Continued)

OTHER PUBLICATIONS

Extended European Search Report dated Feb. 18, 2020 in European Application No. 19195049.2.

*Primary Examiner* — Seyed H Azarian
(74) *Attorney, Agent, or Firm* — Xsensus LLP

(57) ABSTRACT

An ophthalmologic information processing apparatus includes a reference data setting unit, a first region specifying unit, and a second region specifying unit. The reference data setting unit is configured to set, as first reference data, first fundus data among a plurality of fundus data of a fundus of a subject's eye acquired at different acquisition timings using optical coherence tomography. The first region specifying unit is configured to specify one or more first atrophy regions in the fundus by analyzing the first reference data. The second region specifying unit is configured to specify one or more second atrophy regions by analyzing second fundus data based on the one or more first atrophy regions, the second fundus data being acquired after the acquisition timing of the first reference data among the plurality of fundus data.

14 Claims, 16 Drawing Sheets

(51) Int. Cl.
 *A61B 3/12* (2006.01)
 *A61B 3/00* (2006.01)
 *A61B 3/10* (2006.01)
 *G06T 7/00* (2017.01)
(52) U.S. Cl.
 CPC .. *G06T 7/0014* (2013.01); *G06T 2207/10101* (2013.01); *G06T 2207/20036* (2013.01); *G06T 2207/30041* (2013.01)
(58) Field of Classification Search
 USPC ............. 382/219, 254, 276, 286, 305, 312; 351/201, 159.22, 202; 356/3.09, 17, 21
 See application file for complete search history.

(56) References Cited

U.S. PATENT DOCUMENTS

| | | |
|---|---|---|
| 2014/0112562 A1 | 4/2014 | Yamakawa et al. |
| 2014/0118694 A1 | 5/2014 | Fujiu |
| 2015/0201829 A1 | 7/2015 | Yang et al. |
| 2016/0206190 A1* | 7/2016 | Reisman ............. A61B 3/1225 |
| 2017/0065163 A1* | 3/2017 | Yang .................... A61B 5/4842 |
| 2018/0003479 A1* | 1/2018 | Tomatsu ............. G01B 9/02087 |
| 2019/0347796 A1* | 11/2019 | Huang ..................... G06T 7/62 |
| 2020/0046813 A1* | 2/2020 | Borodic ............... A61K 9/0048 |

FOREIGN PATENT DOCUMENTS

| | | |
|---|---|---|
| JP | 2014-83266 A | 5/2014 |
| JP | 2014-83268 A | 5/2014 |
| JP | 2014-90748 A | 5/2014 |
| JP | 2014-527434 A | 10/2014 |
| JP | 2015-136626 A | 7/2015 |
| JP | 2016-107148 A | 6/2016 |
| JP | 2017-87056 A | 5/2017 |

* cited by examiner

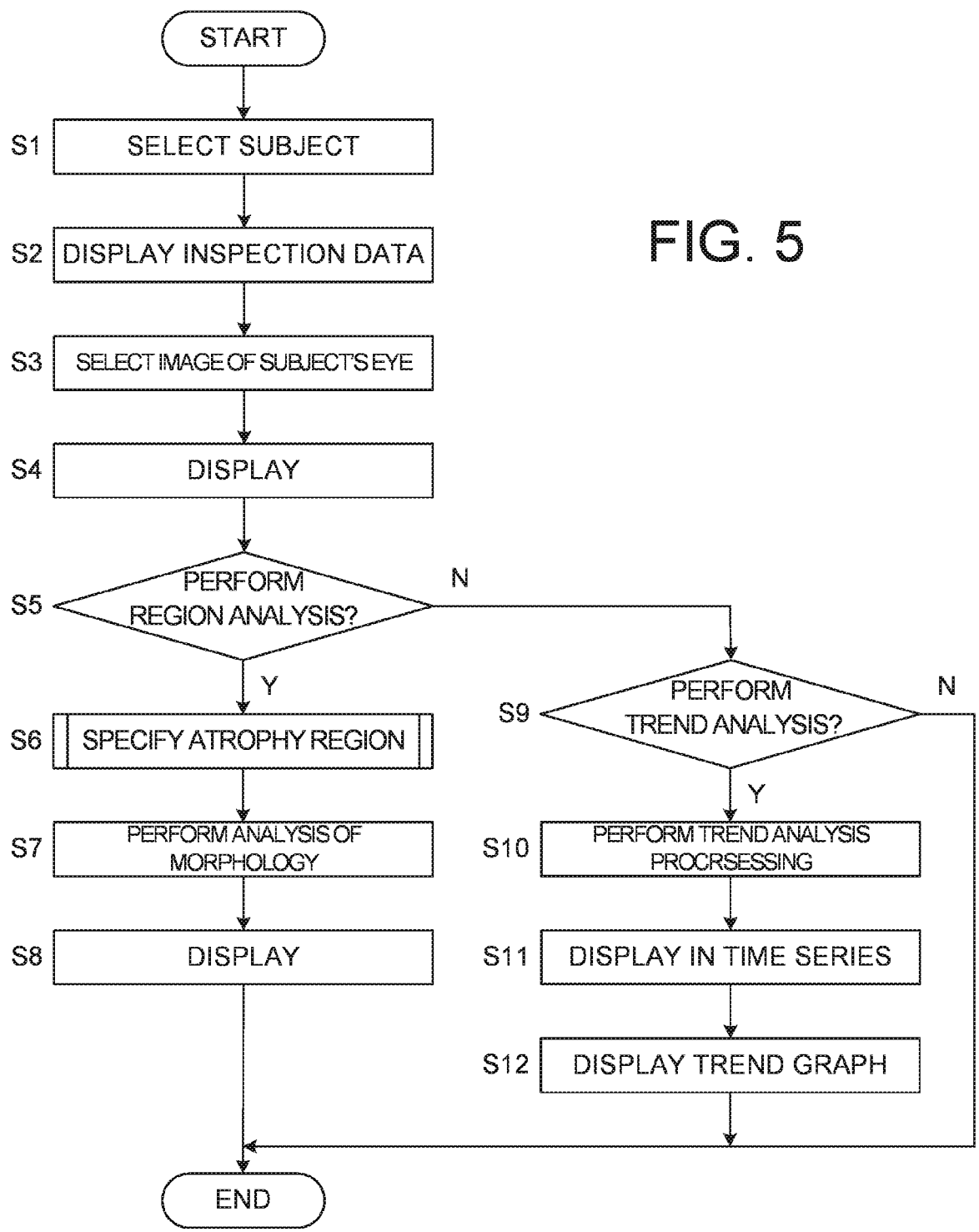

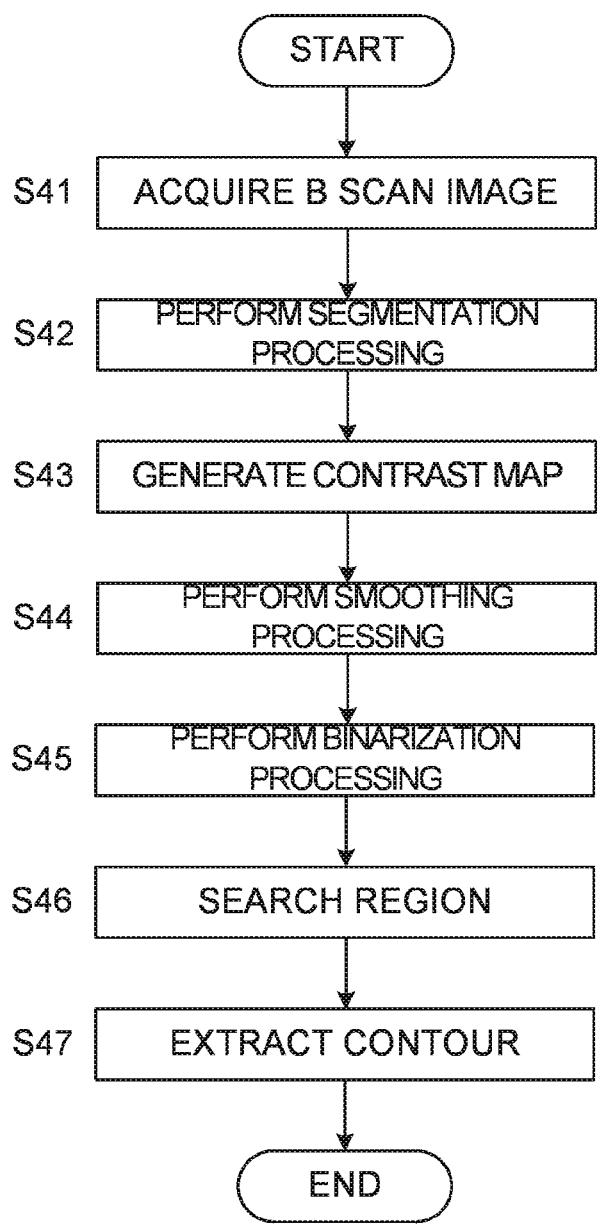

OPHTHALMOLOGIC INFORMATION PROCESSING APPARATUS, OPHTHALMOLOGIC SYSTEM, OPHTHALMOLOGIC INFORMATION PROCESSING METHOD, AND RECORDING MEDIUM

CROSS-REFERENCE TO RELATED APPLICATION

This application is based upon and claims the benefit of priority from Japanese Patent Application No. 2018-179180, filed Sep. 25, 2018; the entire contents of which are incorporated herein by reference.

FIELD

Embodiments according to present invention described herein relate to an ophthalmologic information processing apparatus, an ophthalmologic system, an ophthalmologic information processing method, and a recording medium.

BACKGROUND

Age-related macular degeneration (AMD) is one of the causative diseases of visual disturbance. AMD is a disease in which a macular region is impaired directly or indirectly by aging. AMD is classified into exudative age-related macular degeneration (exudative AMD) and atrophic age-related macular degeneration (atrophic AMD). Exudative AMD is a disease in which a retina is damaged by invasion of choroidal neovascularization from the choroid to the lower layer of retinal pigment epithelium layer (hereinafter, RPE) or invasion of choroidal neovascularization between the retina and the RPE. Atrophic AMD is a disease in which the retina is damaged by gradual atrophy of the RPE and vision is gradually decreased.

Photo dynamic therapy (PDT), drug therapy, laser coagulation and the like are known as effective treatments of exudative AMD. On the other hand, effective treatment for atrophic AMD is not well established at present. Therefore, understanding the state of atrophic AMD is extremely important.

In atrophic AMD, so-called geographic atrophy (GA) is found in a predetermined region centered on a fovea. GA is specified from fundus images, fluorescein fluorescence fundus angiograms, fundus autofluorescence inspection images, or the like, or tomographic images obtained using optical coherence tomography (for example, U.S. Unexamined Patent Application Publication No. 2015/0201829, Japanese Unexamined Patent Application Publication No. 2015-136626, Japanese Unexamined Patent Application Publication No. 2016-107148). The state of atrophic AMD can be understood by observing the specified GA (for example, Japanese Unexamined Patent Application Publication (Translation of PCT Application) No. 2014-505552). Further, a method for facilitating follow-up by displaying trend analysis results of thickness data acquired by analyzing data obtained using optical coherence tomography is disclosed (for example, Japanese Unexamined Patent Application Publication No. 2014-083266 Japanese Unexamined Patent Application Publication No. 2014-083268, Japanese Unexamined Patent Application Publication (Translation of PCT Application) No. 2014-527434, Japanese Unexamined Patent Application Publication No. 2014-090748). In particular, a method for follow-up under different imaging conditions by adding a baseline in Japanese Unexamined Patent Application Publication No. 2014-090748.

SUMMARY

One aspect of some embodiments is an ophthalmologic information processing apparatus including: a reference data setting unit configured to set, as first reference data, first fundus data among a plurality of fundus data of a fundus of a subject's eye acquired at different acquisition timings using optical coherence tomography; a first region specifying unit configured to specify one or more first atrophy regions in the fundus by analyzing the first reference data; and a second region specifying unit configured to specify one or more second atrophy regions by analyzing second fundus data based on the one or more first atrophy regions, the second fundus data being acquired after the acquisition timing of the first reference data among the plurality of fundus data.

Another aspect of some embodiments is an ophthalmologic system including: a data acquisition unit configured to acquire data of the fundus using optical coherence tomography; and the ophthalmologic information processing apparatus described above.

Yet another aspect of some embodiments is an ophthalmologic information processing method including: a reference data setting step that sets, as first reference data, first fundus data among a plurality of fundus data of a fundus of a subject's eye acquired at different acquisition timings using optical coherence tomography; a first region specifying step that specifies one or more first atrophy regions in the fundus by analyzing the first reference data; and a second region specifying step that specifies one or more second atrophy regions by analyzing second fundus data based on the one or more first atrophy regions, the second fundus data being acquired after the acquisition timing of the first reference data among the plurality of fundus data.

Yet another aspect of some embodiments is a non-transitory computer readable recording medium storing a program for causing a computer to execute each step of the ophthalmologic information processing method described above.

BRIEF DESCRIPTION OF THE DRAWINGS

FIG. 5 is a schematic diagram illustrating an example of the operation flow of the ophthalmologic information processing apparatus according to the embodiments.

FIG. 7 is a schematic diagram illustrating an example of the operation flow of the ophthalmologic information processing apparatus according to the embodiments.

DETAILED DESCRIPTION

Figure 1:
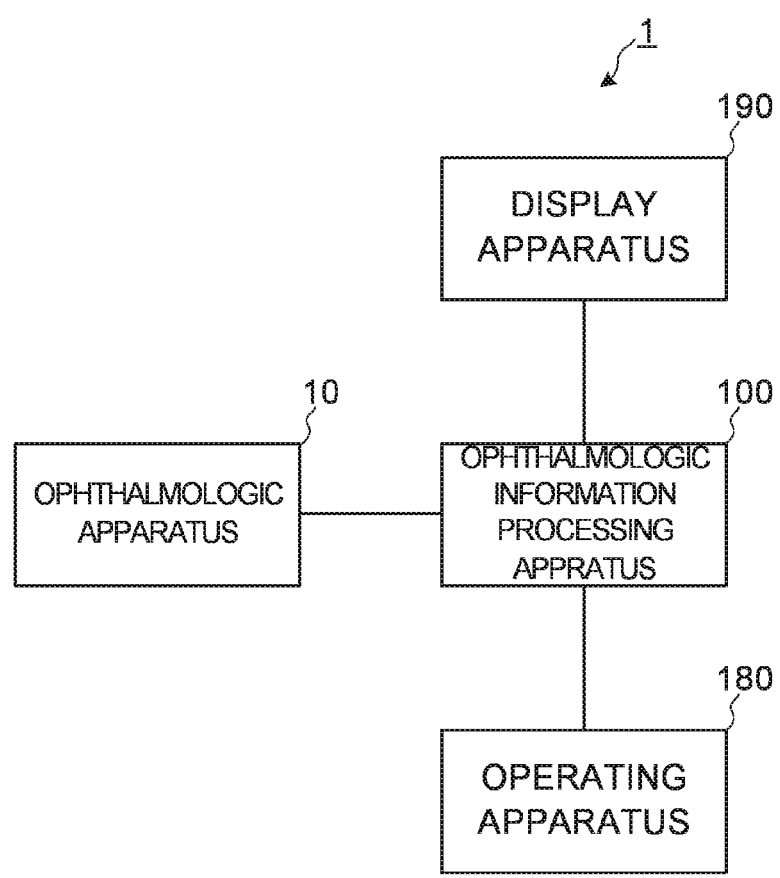
FIG. 1 is a schematic diagram illustrating an example of the configuration of an ophthalmologic system according to embodiments.

In order to understand the state of atrophic AMD (age-related macular degeneration), follow-up of parameters or follow-up of distribution of the parameters is effective, the parameters representing morphology (form) (shape, size) of the region (geographic atrophy region) with geographic atrophy. Therefore, reproducibility parameters to be observed is important for these follow-ups.

At present, there is no effective treatment for geographic atrophy region. It is believed that the geographic atrophy region increases but does not decrease. However, in the prior art, the size of the geographic atrophy region may be detected smaller than in the previous inspection data, thereby it may be difficult to accurately understand a temporal change of the morphology of the geographic atrophy region and the distribution thereof. In this case, a user may be burdened by, for example, prompting the user to correct the detected geographic atrophy region by notifying the user.

According to some embodiments of the present invention, a new technique for accurate follow-up of morphology or distribution of atrophy region on a fundus can be provided while reducing a burden on a user.

Referring now to the drawings, exemplary some embodiments of an ophthalmologic information processing apparatus, an ophthalmologic system, an ophthalmologic information processing method, a program, and a recording medium according to some embodiments of the present invention are described below. Any of the contents of the documents cited in the present specification and arbitrary known techniques may be applied to the embodiments below.

An ophthalmologic system according to the embodiments includes an ophthalmologic information processing apparatus. An ophthalmologic information processing method according to the embodiments is performed by the ophthalmologic information processing apparatus. The ophthalmologic information processing method according to the embodiments can be executed by a computer according to a program.

The ophthalmologic information processing apparatus according to the embodiments can perform predetermined analysis processing and predetermined display processing on data of a fundus of a subject's eye optically acquired using the ophthalmologic apparatus. The ophthalmologic apparatus according to some embodiments has the function of the ophthalmologic information processing apparatus. The ophthalmologic apparatus according to some embodiments has the function of acquiring a front image of the fundus of the subject's eye. Examples of the ophthalmologic apparatus having the function of acquiring the front image of the fundus of the subject's eye include an optical coherence tomography (OCT, hereafter) apparatus, a fundus camera, a scanning laser ophthalmoscope (SLO), a slit lamp microscope, a surgical microscope, and the like. The ophthalmologic apparatus according to some embodiments has the function of measuring optical characteristics of the subject's eye. Examples of the ophthalmologic apparatus having the function of measuring optical characteristics of the subject's eye include a refractometer, a keratometer, a tonometer, a wave front analyzer, a specular microscope, a perimeter, and the like. The ophthalmologic apparatus according to some embodiments has the function of a laser treatment apparatus used for laser therapy.

Ophthalmologic System

FIG. 1 shows a block diagram of an example of the configuration of the ophthalmologic system according to the embodiments. The ophthalmologic system 1 according to the embodiments includes an ophthalmologic apparatus 10, an ophthalmologic information processing apparatus (ophthalmologic image processing apparatus, ophthalmologic analysis apparatus) 100, an operating apparatus 180, and a display apparatus 190.

The ophthalmologic apparatus 10 optically acquires data of the subject's eye. The ophthalmologic apparatus 10 optically acquires the data of the fundus of the subject's eye by scanning the fundus of the subject's eye. For example, the ophthalmologic apparatus 10 acquires three-dimensional OCT data of the fundus of the subject's eye using OCT. The ophthalmologic apparatus 10 can obtain an image of the fundus of the subject's eye from the acquired data of the subject's eye. The images of the fundus include a tomographic image of the fundus, and a front image of the fundus. Examples of the tomographic image of the fundus include a B scan image, and the like. Examples of the front image of the fundus include a C scan image, a shadowgram, a projection image, and the like. The ophthalmologic apparatus 10 sends the acquired data of the subject's eye to the ophthalmologic information processing apparatus 100.

In some embodiments, the ophthalmologic apparatus 10 and the ophthalmologic information processing apparatus 100 are connected via a data communication network. The ophthalmologic information processing apparatus 100 according to some embodiments receives data from one of a plurality of ophthalmologic apparatuses 10 selectively connected via the data communication network.

The ophthalmologic information processing apparatus 100 performs analysis processing on each of a plurality of data in time series of the fundus of the subject's eye acquired on different dates (time or timings) by the ophthalmologic apparatus 10. The ophthalmologic information processing apparatus 100 stores each of the obtained plurality of analysis results in the storage unit (not shown) in association with a subject or a subject's eye and an acquired date (acquired date and time). The ophthalmologic information processing apparatus 100 can control the display apparatus 190 to display the obtained plurality of analysis results in time series. The ophthalmologic information processing apparatus 100 can generate statistical information obtained from the plurality of analysis results. The analysis results include not only information obtained by performing analysis processing but also new information obtained by processing the obtained information.

The ophthalmologic information processing apparatus 100 specifies a geographic atrophy region (atrophy region) by analyzing the data of the subject's eye, and forms an image for identifiably displaying the specified geographic atrophy region. The ophthalmologic information processing apparatus 100 according to some embodiments controls the display apparatus 190 to identifiably display the geographic atrophy region in the front image of the fundus or the tomographic image of the fundus.

The ophthalmologic information processing apparatus 100 obtains parameters representing morphology or distribution of the geographic atrophy region for each of a plurality of geographic atrophy regions specified from a plurality of data of the fundus acquired at different timings. Examples of the parameter include an area of each geographic atrophy region, an outer perimeter of each geographic atrophy region, a total value of area(s) of the geographic atrophy region(s), a total value of outer perimeter(s) of the geographic atrophy region(s), the number of the geographic atrophy regions, a fraction (density) of the geographic atrophy region(s) occupied in a predetermined region, information representing positional relationship of the geographic atrophy region with respect to a reference position, and the like. The ophthalmologic information processing apparatus 100 can control the display apparatus 190 to display the obtained parameters in time series. The ophthalmologic information processing apparatus 100 can control the display apparatus 190 to display statistical information of obtained parameter(s).

The ophthalmologic information processing apparatus 100 can set, as a baseline, at least one of the acquired plurality of data of the fundus, and can set, as baseline data, the geographic atrophy region or the parameter of the geographic atrophy region, the geographic atrophy region being specified from data which is set as the baseline. The ophthalmologic information processing apparatus 100 can specify the geographic atrophy region using the information of the baseline (baseline data) for the data of the fundus acquired after the acquisition timing of the data of the fundus which is set as the baseline. Further, the ophthalmologic information processing apparatus 100 can control the display apparatus 190 to display the geographic atrophy regions or the parameters of the geographic atrophy regions in time series, the geographic atrophy regions being specified from the data acquired after the acquisition timings of the data of the fundus which is set as the baseline.

The operating apparatus 180 and the display apparatus 190 provide the function for exchanging information between the ophthalmologic information processing apparatus 100 and the user, such as displaying information, inputting information, and inputting operation instructions, as a user interface unit. The operating apparatus 180 includes an operating device such as a lever, a button, a key, and pointing device. The operating apparatus 180 according to some embodiments includes a microphone for inputting information using sound. The display apparatus 190 includes a display device such as a flat-panel display. In some embodiments, the function of the operating apparatus 180 and the display apparatus 190 are realized using a device in which a device having an input function such as a touch panel display and a device having a display function are integrated. In some embodiments, the operating apparatus 180 and the display apparatus 190 include a graphical user interface (GUI) for inputting and outputting information.

The ophthalmologic information processing apparatus 100 can control the display apparatus 190 to display parameters in time series, the parameters representing morphology or distribution of one or more geographic atrophy regions designated using the operating apparatus 180 among the specified plurality of geographic atrophy regions. The ophthalmologic information processing apparatus 100 according to some embodiments controls the display apparatus 190 to display statistical information of parameters, the parameters representing morphology or distribution of one or more geographic atrophy regions designated using the operating apparatus 180 among the specified plurality of geographic atrophy regions.

Ophthalmologic Apparatus

Figure 2:
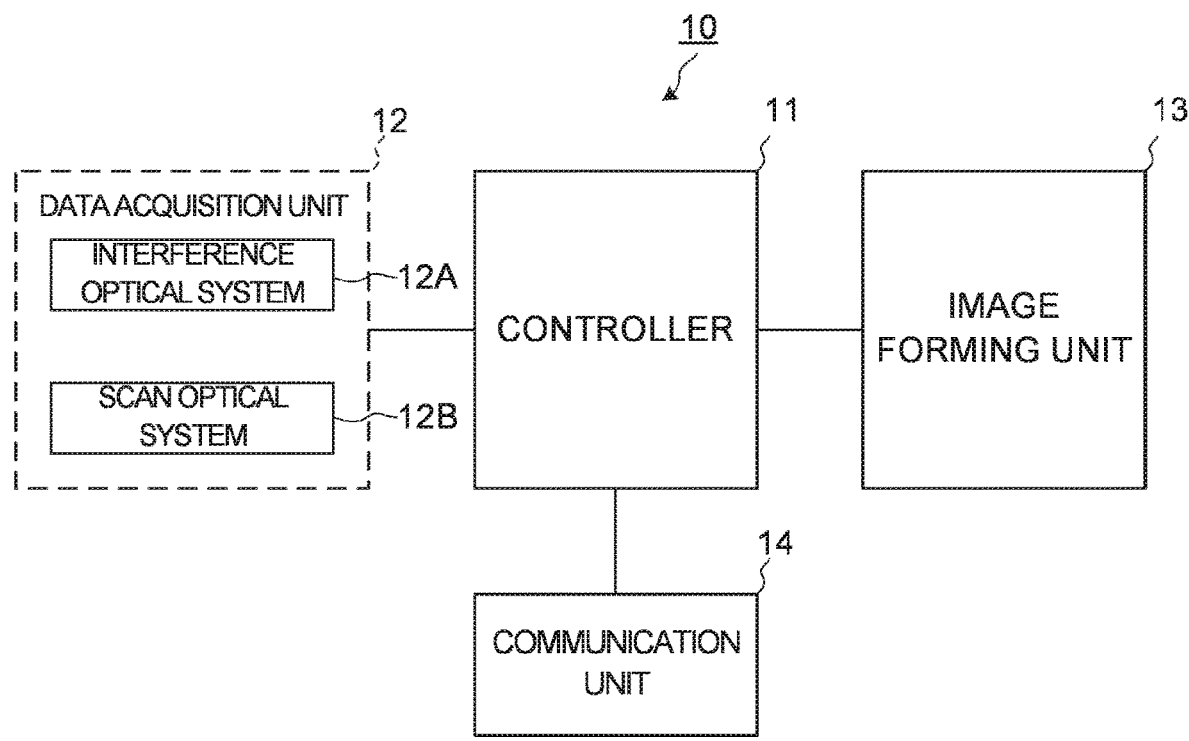
FIG. 2 is a schematic diagram illustrating an example of the configuration of an ophthalmologic apparatus according to the embodiments.

FIG. 2 shows a block diagram of an example of the configuration of the ophthalmologic apparatus 10 according to the embodiments.

The ophthalmologic apparatus 10 includes an optical system for acquiring OCT data of the subject's eye. The ophthalmologic apparatus 10 has a function of performing swept source OCT, but the embodiments are not limited to this. For example, the type of OCT is not limited to swept source OCT, and it may be the spectral domain OCT or the like. The swept source OCT is a technique that splits light from a wavelength tunable type (i.e., a wavelength scanning type) light source into measurement light and reference light; superposes the measurement light returning from the object to be measured with the reference light to generate interference light; detects the interference light with a balanced photodiode or the like; and applies the Fourier transform etc. to the detection data acquired through the tuning of wavelengths and the scanning of the measurement light to form an image. The spectral domain OCT is a technique that splits light from a low coherence light source into measurement light and reference light; superposes the measurement light returning from the object to be measured with the reference light to generate interference light; detects the spectral distribution of the interference light with a spectrometer; and applies the Fourier transform etc. to the detected spectral distribution to form an image.

The ophthalmologic apparatus 10 includes a controller 11, a data acquisition unit 12, an image forming unit 13, and a communication unit 14.

The controller 11 controls each part of the ophthalmologic apparatus 10. In particular, the control unit 11 controls the data acquisition unit 12, the image forming unit 13, and the communication unit 14.

The data acquisition unit 12 acquires data (three-dimensional OCT data) of the subject's eye by scanning the subject's eye using OCT. The data acquisition unit 12 includes an interference optical system 12A and a scan optical system 12B.

The interference optical system 12A splits light from the light source (wavelength scanning type light source) into measurement light and reference light, makes returning light of the measurement light through the subject's eye and the reference light having traveled through a reference optical path interfere with each other to generate interference light, and detects the interference light. The interference optical system 12A includes at least a fiber coupler and a light receiver such as a balanced photodiode. The fiber coupler splits the light from the light source into the measurement light and the reference light, and makes returning light of the measurement light through the subject's eye and the reference light having traveled through a reference optical path interfere with each other to generate interference light. The light receiver detects the interference light generated by the fiber coupler. The interference optical system 12A may include the light source.

The scan optical system 12B changes an incident position of the measurement light on the fundus of the subject's eye by deflecting the measurement light generated by the interference optical system 12A, under the control of the controller 11. The scan optical system 12B includes, for example, an optical scanner disposed at a position optically conjugate with a pupil of the subject's eye E. The optical scanner includes, for example, a galvano mirror that scans with the measurement light in the horizontal direction, a galvano mirror that scans with the measurement light in the vertical direction, and a mechanism that independently drives the galvano mirrors. With this, it is possible to scan the measurement light in an arbitrary direction in the fundus plane.

A detection result (detection signal) of the interference light obtained by the interference optical system 12A is an interference signal representing the spectrum of the interference light.

The image forming unit 13 forms image data of a tomographic image of the fundus of the subject's eye based on the data of the subject's eye acquired by the data acquisition unit 12, under the control of the controller 11. This processing includes noise removal (noise reduction), filtering, fast Fourier transform (FFT), and the like. The image data acquired in this manner is a data set including a group of image data formed by imaging the reflection intensity profiles of a plurality of A lines. Here, the A lines are the paths of the measurement light in the subject's eye. In order to improve the image quality, it is possible to repeatedly perform scan with the same pattern a plurality of times to collect a plurality of data sets, and to compose (i.e., average) the plurality of data sets.

The image forming unit 13 can form a B scan image, a C scan image, a projection image, a shadowgram, etc., by performing various renderings on the acquired three-dimensional OCT data. An image in an arbitrary cross section such as the B scan image or the C scan image is formed by selecting pixels (voxels) on a designated cross section from the three-dimensional OCT data. The projection image is formed by projecting the three-dimensional OCT data in a predetermined direction (Z direction, depth direction, A scan direction). The shadowgram is formed by projecting a part of the three-dimensional OCT data (for example, partial data corresponding to a specific layer) in a predetermined direction.

The ophthalmologic apparatus 10 according to some embodiments includes a data processor that performs various kinds of data processing (e.g., image processing) and various kinds of analysis processing on the image formed by the image forming unit 13. For example, the data processor performs various correction processes such as brightness correction and dispersion correction of images. The data processor can form volume data (voxel data) of the subject's eye by performing known image processing such as interpolation processing for interpolating pixels between tomographic images. In the case of displaying an image based on the volume data, the data processor performs rendering processing on the volume data so as to form a pseudo three-dimensional image viewed from a specific line-of-sight direction.

Each of the controller 11 and the image forming unit 13 includes a processor. The processor includes, for example, a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The functions of the image forming unit 13 are realized by an image forming processor. In some embodiments, both of the functions of the controller 11 and the image forming unit 13 are realized by a single processor. In some embodiments, in case that the ophthalmologic apparatus 10 includes the data processor, the functions of the data processor are also realized by a processor.

The processor realizes, for example, the function according to the embodiments by reading out a computer program stored in a storage circuit or a storage apparatus and executing the computer program. At least a part of the storage circuit or the storage apparatus may be included in the processor. Further, at least a part of the storage circuit or the storage apparatus may be provided outside of the processor.

The storage apparatus etc. stores various types of data. Examples of the data stored in the storage apparatus etc. include data (measurement data, photographic data, etc.) acquired by the data acquisition unit 12 and information related to the subject and the subject's eye. The storage apparatus etc. may store a variety of computer programs and data for the operation of each part of the ophthalmologic apparatus 10.

The communication unit 14 performs communication interface processing for sending or receiving information with the ophthalmologic information processing apparatus 100 under the control of the controller 11.

The ophthalmologic apparatus 10 according to some embodiments sends the image data of the subject's eye formed by the image forming unit 13 to the ophthalmologic information processing apparatus 100.

The ophthalmologic apparatus 10 according to some embodiments includes a fundus camera for acquiring an image of the fundus of the subject's eye, a scanning laser ophthalmoscope for acquiring an image of the fundus of the subject's eye, or a slit lamp microscope. In some embodiments, the fundus image acquired by the fundus camera is a fluorescein fluorescence fundus angiogram or a fundus autofluorescence inspection image.

Ophthalmologic Information Processing Apparatus

Figure 3:
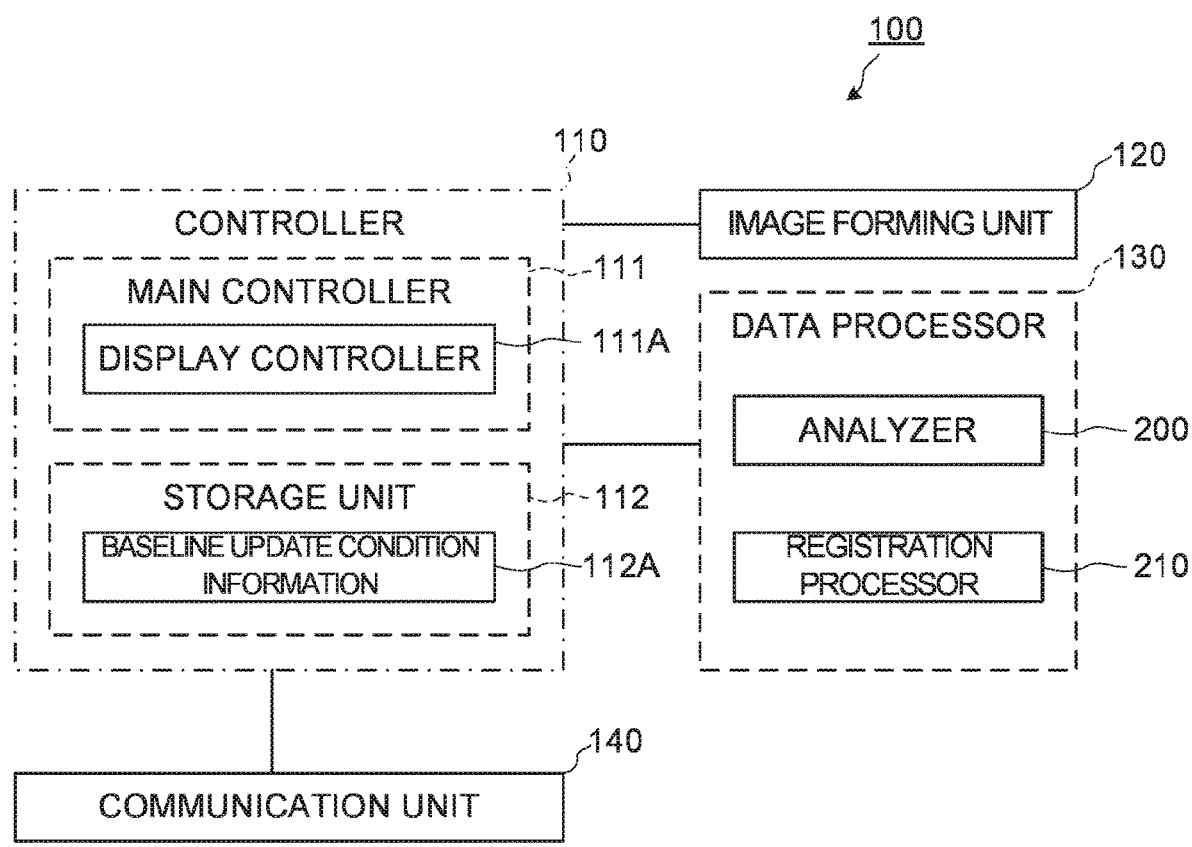
FIG. 3 is a schematic diagram illustrating an example of the configuration of an ophthalmologic information processing apparatus according to the embodiments.
Figure 4:
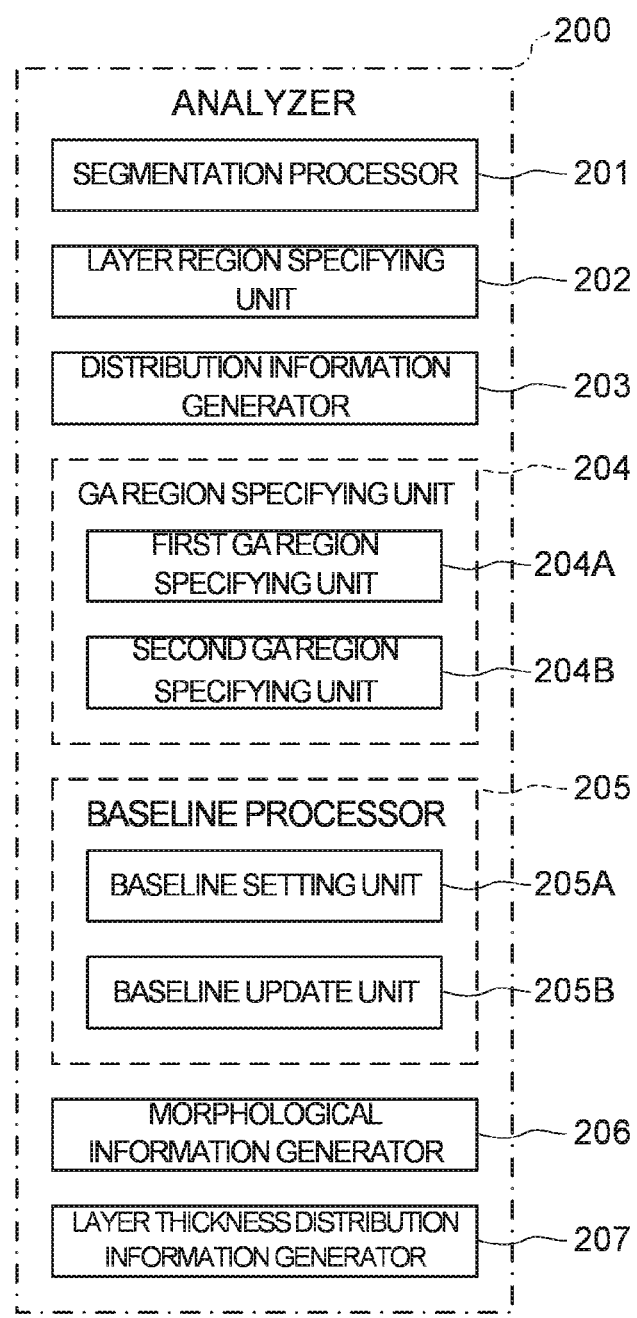
FIG. 4 is a schematic diagram illustrating an example of the configuration of the ophthalmologic information processing apparatus according to the embodiments.

FIGS. 3 and 4 show block diagrams of examples of the configuration of the ophthalmologic information processing apparatus 100 according to the embodiments. FIG. 3 shows a functional block diagram of the ophthalmologic information processing apparatus 100. FIG. 4 shows a functional block diagram of an analyzer 200 of FIG. 3.

The ophthalmologic information processing apparatus 100 performs analysis processing on each of the plurality of data in time series of the fundus of the subject's eye acquired on different dates by the ophthalmologic apparatus 10. The ophthalmologic information processing apparatus 100 stores each of the plurality of analysis results obtained by performing analysis processing in a storage unit 112 described after, in association with the subject or the subject's eye and an inspection date (inspection date and time). The ophthalmologic information processing apparatus 100 according to some embodiments stores each of the obtained plurality of analysis results in the storage apparatus connected via a predetermined network, in association with the subject's eye and the inspection date. The plurality of analysis results obtained by performing analysis processing is displayed in time series by the ophthalmologic information processing apparatus 100.

The ophthalmologic information processing apparatus 100 analyzes the data of the fundus of the subject's eye acquired by the ophthalmologic apparatus 10 to specify a geographic atrophy region on the fundus. The ophthalmologic information processing apparatus 100 causes the display apparatus 190 to display the specified geographic atrophy region in the front image or the tomographic image of the fundus in an identifiable manner.

The ophthalmologic information processing apparatus 100 causes the display apparatus 190 to display, in time series, images representing the plurality of geographic atrophy regions specified based on the plurality of the data of the fundus of the subject's eye with different inspection dates. The ophthalmologic information processing apparatus 100 obtains parameters representing morphology or distribution of the geographic atrophy region for each of the specified plurality of geographic atrophy regions, and causes the display apparatus 190 to display the obtained parameters in time series. The ophthalmologic information processing apparatus 100 can set, as a baseline, at least one of the plurality of data of the fundus with different inspection dates. The ophthalmologic information processing apparatus 100 can specify the geographic atrophy region or the parameter thereof using the information of the baseline, the geographic atrophy region being specified from one or more data of the fundus acquired after the acquisition timing of the data of the fundus set as the baseline. Further, the ophthalmologic information processing apparatus 100 can cause the display apparatus 190 to display, in time series, the baseline data and the geographic atrophy region(s) or the parameter(s) thereof, the geographic atrophy region(s) being specified based on the data of the fundus acquired after the baseline. Here, the baseline data includes the geographic atrophy region(s) or the parameters thereof, the geographic atrophy region(s) being specified from the data of the fundus set as the baseline.

The baseline is updated when a predetermined baseline update condition is satisfied. The ophthalmologic information processing apparatus 100 can specify the geographic atrophy region using the information of the updated baseline for the data of the fundus acquired after the acquisition timing of the data of the fundus set as the updated baseline. The ophthalmologic information processing apparatus 100 can cause the display apparatus 190 to display, in time series, the one or more geographic atrophy regions or the parameters thereof on the bases of the updated baseline data. Here, the one or more geographic atrophy regions are specified from the one or more data of the fundus acquired after updating the baseline data.

The ophthalmologic information processing apparatus 100 causes the display apparatus 190 to display statistical information of the obtained parameter(s).

The ophthalmologic information processing apparatus 100 includes a controller 110, an image forming unit 120, a data processor 130, and a communication unit 40.

The image forming unit 120 forms a B scan image, a C scan image, a projection image, a shadowgram, or the like from the three-dimensional OCT data acquired by the ophthalmologic apparatus 10 under the control of the controller 110. The image forming unit 120 can form the above image in the same manner as the image forming unit 13.

The data processor 130 performs various kinds of data processing (e.g., image processing) and various kinds of analysis processing on an image formed by the image forming unit 120. For example, the data processor 130 performs various correction processes such as brightness correction and dispersion correction of images. The data processor 130 can form volume data (voxel data) of the subject's eye E by performing known image processing such as interpolation processing for interpolating pixels between tomographic images. In the case of displaying an image based on the volume data, the data processor 130 performs a rendering processing on the volume data so as to form a pseudo three-dimensional image viewed from a specific line-of-sight direction.

The data processor 130 performs predetermined data processing on the formed image of the subject's eye. The processing unit 130 includes the analyzer 200 and a registration processor 210.

The analyzer 200 performs predetermined analysis processing on the image data of the fundus of the subject's eye formed by the image forming unit 120 (or the image data of the fundus of the subject's eye acquired by the ophthalmologic apparatus 10). Examples of the analysis processing according to some embodiments include specifying processing of the geographic atrophy region on the fundus, setting processing and updating processing of the baseline, generating processing of the distribution information of the geographic atrophy region, generating processing of the morphological information of the geographic atrophy region, statistical processing of the distribution information or the morphological information, generating processing of the distribution information of layer thickness in the fundus, and the like.

The analyzer 200 include a segmentation processor 201, a layer region specifying unit 202, a distribution information generator 203, a GA region specifying unit 204, a baseline processor 205, a morphological information generator 206, and a layer thickness distribution information generator 207. The GA region specifying unit 204 includes a first GA region specifying unit 204A and a second GA region specifying unit 204B. The baseline processor 205 includes a baseline setting unit 205A and a baseline update unit 205B. Each part of the analyzer 200 performs the following processing on each of the plurality of data of the fundus of the subject's eye.

The segmentation processor 201 specifies a plurality of layer regions in the A scan direction based on the data of the subject's eye acquired by the ophthalmologic apparatus 10. The segmentation processor 201 according to some embodiments analyzes the three-dimensional OCT data to specify a plurality of partial data sets corresponding to a plurality of tissues of the subject's eye. The segmentation processing is image processing for specifying specific tissues and/or tissue boundaries. For example, the segmentation processor 201 obtains the gradients of the pixel values (i.e., brightness values) in each A scan image included in the OCT data, and specifies a position where the gradient value is large to be a tissue boundary. Note that the A scan image is one-dimensional image data extending in the depth direction of the fundus. The depth direction of the fundus is defined as, for example, the Z direction, the incident direction of the OCT measurement light, the axial direction, the optical axis direction of the interference optical system, or the like.

In a typical example, the segmentation processor 201 specifies a plurality of partial data sets corresponding to a plurality of layer tissues of the fundus by analyzing the three-dimensional OCT data representing the fundus (the retina, the choroid, etc.) and the vitreous body. Each partial data set is defined by the boundaries of the layer tissue. Examples of the layer tissue specified as the partial data set include a layer tissue constituting the retina. Examples of the layer tissue constituting the retina include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, and the like. The segmentation processor 201 can specify a partial data set corresponding to the Bruch membrane, the choroid, the sclera, the vitreous body, or the like. The segmentation processor 201 according to some embodiments specifies a partial data set corresponding to the site of lesion. Examples of the site of lesion include a detachment part, an edema, a bleeding site, a tumor, a drusen, and the like.

The segmentation processor 201 according to some embodiments specifies, as the Bruch membrane, a layer tissue for a predetermined number of pixels on the sclera side with respect to the RPE, and acquires, as the partial data set of the Bruch membrane, the partial data set corresponding to the layer tissue.

The layer region specifying unit 202 specifies a region corresponding to two layer tissues for specifying the geographic atrophy region by analyzing a plurality of partial data sets of the layer tissues specified by the segmentation processor 201. The layer region specifying unit 202 according to some embodiments specifies a first region and a second region, the first region corresponding to a layer tissue on the sclera side from a region corresponding to the Bruch membrane, the second region corresponding to a layer region from a region corresponding to the inner limiting membrane to a region corresponding to the RPE. In some embodiments, the second region is a region corresponding to a layer tissue on the cornea side from the region corresponding to the Bruch membrane.

The distribution information generator 203 obtains a contrast ratio for each A scan based on the pixel values in the first region and the second region which are specified by the layer region specifying unit 202, and generates two-dimensional distribution information of the contrast ratio in the fundus plane (plane orthogonal to the A scan direction). In some embodiments, the distribution information generator 203 generates the distribution information of the ratio of the integrated value of the pixel values of the first region specified by the layer region specifying unit 202 and the integrated value of the pixel values of the second region specified by the layer region specifying unit 202, for each A scan. The distribution information generator 203 according to some embodiments obtains, as the contrast ratio, the ratio of the integrated value of the pixel values in the A scan direction of the second region to the integrated value of the pixel values in the A scan direction of the first region, and generates the two-dimensional distribution information of the obtained contrast ratio. The two-dimensional distribution information of the contrast ratio is hereinafter referred to as a contrast map.

The GA region specifying unit 204 specifies the geographic atrophy region. The first GA region specifying unit 204A specifies the geographic atrophy region by analyzing the OCT data of the fundus. The second GA region specifying unit 204B specifies the geographic atrophy region from the OCT data of the fundus different from the OCT data to be processed by the first GA region specifying unit 204A, using the processing result by the first GA region specifying unit 204A or information during processing of the first GA region specifying unit 204A.

The first GA region specifying unit 204A specifies, for example, a position where the contrast ratio is large, as a position where signal components are attenuated due to the geographic atrophy in the contrast map generated by the distribution information generator 203. The first GA region specifying unit 204A specifies the geographic atrophy region based on the specified position. For example, the first GA region specifying unit 204A specifies, as the geographic atrophy region, a region including positions where the contrast ratio are equal to or larger than a predetermined threshold value, in the contrast map generated by the distribution information generator 203. Techniques related to such a method for specifying a geographic atrophy region are disclosed in U.S. Unexamined Patent application Publication No. 2015/0201829, Japanese Unexamined Patent Application Publication No. 2015-136626, or Japanese Unexamined Patent Application Publication No. 2016-107148.

The second GA region specifying unit 204B specifies the geographic atrophy region (second atrophy region) from the data of the fundus of the subject's eye acquired after the baseline (first reference data) set by the baseline setting unit 205A described after, using the geographic atrophy region or the parameter(s) thereof specified from the baseline. Further, the second GA region specifying unit 204B specifies the geographic atrophy region (second atrophy region) from the data of the fundus of the subject's eye acquired after the baseline (second reference data) updated by the baseline update unit 205B described after, using the geographic atrophy region or the parameter(s) thereof specified from the updated baseline.

The second GA region specifying unit 204B can specify one or more new geographic atrophy regions (second atrophy region). Here, the one or more new geographic atrophy regions are obtained by connecting a region, which has the same characteristic amount as in the geographic atrophy region specified by the first GA region specifying unit and is adjacent to the geographic atrophy region, to the geographic atrophy region. In some embodiments, the connected region is displayed on the display apparatus 190 in an identifiable manner.

For example, the second GA region specifying unit 204B obtains a difference between the baseline data and the OCT data to be processed which have been performed position matching, and specifies, as the new geographic atrophy region, a region in which the obtained difference is substantially the same as the difference in the geographic atrophy region.

Alternatively, for example, the second GA region specifying unit 204B specifies a region corresponding to the geographic atrophy region specified from the OCT data to be processed by the first GA region specifying unit 204A, and performs extension processing for extending the region on the image representing the specified region. Thereby, in case that the region having the same characteristics amount as that in the geographic atrophy region specified by the first GA region specifying unit 204A is adjacent, the geographic atrophy region is extended. And in case that the region having the same characteristics amount as that in the geographic atrophy region is not adjacent, the geographic atrophy region is not extended.

As such extension processing, processing of setting a seed pixel at the boundary of the specified region, labeling surround pixels having substantially the same pixel value as the seed pixel as the same region, connecting the labeled region, and the like is known. In some embodiments, the pixel at the boundary of the region obtained as the result (for example, the above distribution information) during specifying processing of the geographic atrophy region by the first GA region specifying unit 204A may set as the seed pixel, and the region may be extended at the result during processing. It should be noted that the extension processing may be known contour tracking processing, a snake method, a clustering method such as a mean shift method.

The baseline processor 205 performing setting and updating of the baseline which is a reference data for the follow-up.

The baseline setting unit 205A sets, as the baseline, one or more data of the fundus among the plurality of data of the fundus with different inspection dates, and sets, as the baseline data, the geographic atrophy region or the parameter(s) thereof, the geographic atrophy region being specified from the data of the fundus set as the baseline. The above first GA region specifying unit 204A can perform specifying processing of the geographic atrophy region on the data of the fundus set as the baseline by the baseline setting unit 205A, and can specify the one or more geographic atrophy regions or the parameters thereof. In some embodiments, the baseline setting unit 205A sets two or more baselines.

The baseline update unit 205B can update the baseline set by the baseline setting unit 205A, based on the geographic atrophy region or the parameters thereof, the geographic atrophy region being specified by the GA region specifying unit 204. Specifically, the baseline update unit 205B can update the baseline set by the baseline setting unit 205A, based on the one or more geographic atrophy regions specified by the first GA region specifying unit 204A and the one or more geographic atrophy regions specified by the second GA region specifying unit 204B. For example, the baseline update unit 205B updates the baseline (i.e., the baseline data) based on at least one of the number of the geographic atrophy region(s), the area of the geographic atrophy region(s), or the perimeter of the geographic atrophy region(s), the geographic atrophy region(s) being specified by the GA region specifying unit 204. The area of the geographic atrophy region(s) may be a total area of the geographic atrophy regions specified by the GA region specifying unit 204, an area of the predetermined one or more geographic atrophy regions among the specified geographic atrophy regions, or an area (maximum value, average value, median value, or the like of area of each region) of geographic atrophy region(s) statistically specified among the specified geographic atrophy regions. The perimeter of the geographic atrophy region(s) may be a total perimeter of the geographic atrophy regions specified by the GA region specifying unit 204, a perimeter of the predetermined one or more geographic atrophy regions among the specified geographic atrophy regions, or a perimeter (maximum value, average value, median value, or the like of perimeter of each region) of geographic atrophy region(s) statistically specified among the specified geographic atrophy regions.

In the embodiment, the update condition of the baseline is set in advance. The baseline update condition information 112A for defining the update condition of the baseline is stored in the storage unit 121 in advance. The baseline update unit 205B updates the baseline when the baseline update condition defined in the baseline update condition information 112A stored in the storage unit 121 is satisfied. Thereby, the data of the fundus of the inspection date (inspection timing) different from the baseline set by the baseline setting unit 205A can be set as a new baseline.

The baseline update condition is set based on temporal change in the above parameter(s) with respect to the baseline date. In some embodiments, the baseline update condition is that the number satisfying a plurality of condition items is equal to or greater than a first threshold value. The first threshold value may be a value set in advance or a value set by the user.

For example, the plurality of condition items are the following (a) to (c).

(a) Assuming that an increase amount of the area of the geographic atrophy region(s) on the basis of the baseline data is $\Delta GA$ and a second threshold value is TH2, $\Delta GA \geq TH2$.

(b) Assuming that an increase amount of the perimeter of the geographic atrophy region(s) on the basis of the baseline data is $\Delta GL$ and a third threshold value is TH3, $\Delta GL \geq TH3$.

(c) The number of the geographic atrophy region(s) changes on the basis of the baseline data.

It should be noted that at least one of the second threshold value TH2 or the third threshold value TH3 may be a value set in advance or a value set by the user.

In some embodiments, new data of the fundus is designated as a new baseline according to the content of the user's operation on the operating apparatus 180. The baseline update unit 205B can set, as the new baseline, the data of the fundus designated by the user using the operating apparatus 180.

The morphological information generator 206 generates morphological information representing morphology of the geographic atrophy region specified by the GA region specifying unit 204. Examples of the morphological information include the area of the geographic atrophy region(s), the outer perimeter of the geographic atrophy region(s), and the like. The morphological information generator 206 can obtain the area of the geographic atrophy region(s) or the outer perimeter of the geographic atrophy region(s) by applying a known method to the image in which the geographic atrophy region(s) is(are) depicted. The morphological information generator 206 according to some embodiments generates the morphological information for each of the specified geographic atrophy regions. The morphological information generator 206 according to some embodiments generates, as the morphological information, the total value of morphological parameters (area, outer perimeter) for each of the specified geographic atrophy region(s). In some embodiments, the morphological information includes the number of the specified geographic atrophy regions.

The layer thickness distribution information generator 207 specifies a thickness in the A scan direction of each of the layer tissues by analyzing the partial data sets of the plurality of the layer tissues specified by the segmentation processor 201, and generates the two-dimensional distribution information of the layer thickness of the each layer in the fundus plane. The layer thickness distribution information generator 207 according to some embodiments generates the two-dimensional distribution information (distribution information of the plane orthogonal to the A scan direction) of the layer thickness of the one or more layer tissues designated using the operating apparatus 180. The layer thickness distribution information generator 207 according to some embodiments generates the two-dimensional distribution information of the layer thickness of at least one of the inner limiting membrane, the nerve fiber layer (NFL), the ganglion cell layer (GCL), the inner plexiform layer (IPL), the inner nuclear layer (INL), the outer plexiform layer (OPL), the outer nuclear layer (ONL), the external limiting membrane (ELM), the retinal pigment epithelium layer (RPE), the choroid, the sclera, or the choroidal-scleral interface (CSI), or two or more adjacent layers.

The analyzer 200 performs trend analysis processing based on a plurality of analysis processing results obtained by performing the above analysis processing on each of the plurality of data of the fundus of the subject's eye. The trend analysis processing includes processing for generating information indicating temporal change of the plurality of analysis processing results. Examples of the information indicating temporal change include a graph in which each analysis processing result is plotted in chronological order, an analysis map representing the distribution of the analysis processing result at each position in the fundus plane, and the like. In some embodiments, the information indicating temporal change includes a regression line or a regression curve obtained by regression analysis, a p-value, a predicted value of the analysis result at predetermined future time, event information, information indicating temporal change based on normal eye data, and the like. In some embodiments, a target for the analysis processing is designated using the operating apparatus 180.

The registration processor 210 performs registration (position matching) between a front image of the fundus formed by the image forming unit 120 and an image representing the geographic atrophy region specified by the analyzer 200. The registration processor 210 performs registration between the tomographic image of the fundus formed by the image forming unit 120 and the image representing the geographic atrophy region specified by the analyzer 200. The registration processor 210 can perform registration using known processing such as affine transformation for performing enlargement, reduction, rotation, or the like of the image.

The registration processing includes, for example, processing for detecting characteristic sites from the both images and processing for performing registration of the both images on the base of the both characteristic sites. In some embodiments, the registration processing includes processing for specifying a position in the image representing the geographic atrophy region in the front image or the tomographic image using position information of the geographic atrophy region in the front image or the tomographic image of the fundus and processing for performing registration of the image representing the specified geographic atrophy region with respect the front image or the tomographic image.

The communication unit 140 performs communication interface processing for sending or receiving information with the communication unit 14 of the ophthalmologic information processing apparatus 100 under the control of the controller 110.

The controller 110 controls each part of the ophthalmologic information processing apparatus 100. In particular, the controller 110 controls the image forming unit 120, the data processor 130, and the communication unit 140. The controller 110 includes the main controller 111 and a storage unit 112. The main controller 111 includes the display controller 111A.

The display controller 111A causes the display apparatus 190 to display the various information. For example, the display controller 111A controls the display apparatus 190 to display the fundus image (front image, tomographic image) of the subject's eye formed by the image forming unit 120 or the image of the data processing result (including the analysis processing result) by the data processor 130. In particular, the display controller 111A causes the display apparatus 190 to display the fundus image of the subject's eye, and to display the region corresponding to the geographic atrophy region in the fundus image in an identifiable manner. The display controller 111A according to some embodiments causes the display apparatus 190 to display the fundus image of the subject's eye, and to display the region corresponding to the geographic atrophy region in the fundus image with high-light. For example, the display controller 111A controls the display apparatus 190 to display the geographic atrophy region or its background region such that the brightness of the pixels in the geographic atrophy region or its background region is higher than the brightness of the pixels in the other regions. The display controller 111A according to some embodiments causes the display apparatus 190 to display an image in which the image representing the geographic atrophy region performed registration by the registration processor 210 is overlaid on the fundus image.

Further, the display controller 111A can cause the display apparatus 190 to display, in time series, the images representing the geographic atrophy regions specified from the plurality of the data of the fundus with different inspection dates. The display controller 111A according to some embodiments causes the display apparatus 190 to display, in time series, a plurality of geographic atrophy region images. In each of the plurality of geographic atrophy region images, the image representing the geographic atrophy region in which registration is performed by the registration processor 210 is overlaid on the fundus image or the tomographic image.

Further, the display controller 111A causes the display apparatus 190 to display the morphological information generated by the morphological information generator 206. For example, the morphological information generator 206 generates the morphological information on each of the plurality of data of the fundus. The display controller 111A controls the display apparatus 190 to display a first time-series information and a second time-series information on the same screen. Here, the first time-series information is time-series information of a plurality of morphological information corresponding to the data of the fundus acquired after the acquisition timing of the baseline with reference to the morphological information of the baseline set by the baseline setting unit 205A. The second time-series information is time-series information of a plurality of morphological information corresponding to the data of the fundus acquired after the acquisition timing of the updated baseline with reference to the morphological information of the baseline updated by the baseline update unit 205B.

The display controller 111A according to some embodiments controls the display apparatus 190 to display the morphological information generated by the morphological information generator 206 in association with the geographic atrophy region corresponding to the morphological information. The display controller 111A according to some embodiments causes the display apparatus 190 to display, in time series, a plurality of morphological information generated based on the time-series plurality of the data of the fundus by the morphological information generator 206. The display controller 111A according to some embodiments causes the display apparatus 190 to display the morphological information (the morphological information of each geographic atrophy region, the total value of the morphological information of the one or more geographic atrophy regions) in time series. Here, the morphological information corresponds to the one or more geographic atrophy regions for each of the one or more geographic atrophy regions designated using the operating apparatus 180.

The controller 110 controls each part of the ophthalmologic system 1 based on operation signal corresponding to the operation content of the user on the operating apparatus 180.

Each of the controller 110, the image forming unit 120, and the data processor 130 includes a processor. The functions of the image forming unit 120 is realized by a processor. The functions of the data processor 130 is realized by a processor. In some embodiments, at least two functions of the controller 110, the image forming unit 120, and the data processor 130 are realized by a single processor.

The storage unit 112 stores various kinds of data including the above baseline update condition information 112A. Examples of the data stored in the storage unit 112 include data (measurement data, photographic data, etc.) acquired by the ophthalmologic apparatus 10, image data formed by the image forming unit 120, data processing result(s) by the data processor 130, information related to the subject and the subject's eye, and the like. The storage unit 112 may store a variety of computer programs and data for the operation of each part of the ophthalmologic information processing apparatus 100.

The baseline setting unit 205A is an example of the "reference data setting unit" according to the embodiments. The first GA region specifying unit 204A (GA region specifying unit 204) is an example of the "first region specifying unit" according to the embodiments. The second GA region specifying unit 204B (GA region specifying unit 204) is an example of the "second region specifying unit" according to the embodiments. The baseline update unit 205B is an example of the "reference data update unit" according to the embodiments. The operating apparatus 180 is an example of the "operation unit" according to the embodiments. The display apparatus 190 is an example of "display means" according to the embodiments. The geographic atrophy region is an example of the "atrophy region" according to the embodiments.

Operation Example

Examples of the operation of the ophthalmologic information processing apparatus 100 according to some embodiments will be described.

FIGS. 5 to 7 show examples of the operation of the ophthalmologic information processing apparatus 100 according to the embodiments. FIG. 5 shows a flowchart of an example of the operation of the ophthalmologic information processing apparatus 100. FIG. 6 shows a flowchart of an example of the operation of step S6 in FIG. 5. FIG. 7 shows a flowchart of an example of the operation of step S24 in FIG. 6. The storage unit 112 stores computer programs for realizing the processing shown in FIGS. 5 to 7. The main controller 111 operates according to the computer programs, and thereby the main controller 111 performs the processing shown in FIGS. 5 to 7.

In FIG. 5, it is assumed that the three-dimensional OCT data of the subject's eye acquired by the ophthalmologic apparatus 10 is already stored in the ophthalmologic information processing apparatus 100 (storage unit 112).

S1: Select Subject

The user selects a subject by inputting the subject ID using the operating apparatus 180.

S2: Display Inspection Data

The storage unit 112 stores a database in which the inspection data of the subject is associated in advance corresponding to the subject ID. The controller 110 searches the database using the subject ID input in step S1 as a search key, and acquires the inspection data corresponding to the subject ID. The display controller 111A causes the display apparatus 190 to display the inspection data corresponding to the subject ID acquired by searching the database. The inspection data includes one or more fundus images of the subject's eye acquired in the past inspection.

S3: Select Image of Subject's Eye

The ophthalmologic information processing apparatus 100 causes the user to select the image of the subject's eye to be analyzed among the one or more images of the subject's eye in the inspection data of the subject displayed on the display apparatus 190 in step S2. The subject (i.e., the user) operates the operating apparatus 180 to select the image of the subject's eye to be analyzed. The controller 110 receives the operation instruction signal corresponding to the operation content of the operating apparatus 180 by the user.

S4: Display

The display controller 111A selects the image of the subject's eye designated based on the operation instruction signal input in step S3 to cause the display apparatus 190 to display the selected image of the subject's eye.

S5: Perform Region Analysis?

Next, the controller 110 determines whether or not to perform analysis of the geographic atrophy region on the image of the subject's eye displayed in step S4. The controller 110 can determine whether or not to perform analysis of the geographic atrophy region based on the operation instruction signal corresponding to the operation content on the operating apparatus 180.

When it is determined that the analysis of the geographic atrophy region is to be performed (S5: Y), the operation of the ophthalmologic information processing apparatus 100 proceeds to step S6. When it is determined that the analysis of the geographic atrophy region is not to be performed (S5: N), the operation of the ophthalmologic information processing apparatus 100 proceeds to step S9.

S6: Specify Atrophy Region

When it is determined that the analysis of the geographic atrophy region is to be performed in step S5 (S5: Y), the controller 110 controls the analyzer 200 to specify the geographic atrophy region by performing analysis of the geographic atrophy region. Details of step S6 will be described later. The controller 110 stores region specific information for specifying a position and a shape of the geographic atrophy region on the fundus in association with the subject or the subject's eye and the inspection date in the storage unit 112.

S7: Perform Analysis of Morphology

Sequentially, the controller 110 controls the morphological information generator 206 to calculate an area and an outer perimeter of each of the geographic atrophy regions specified in step S6. The morphological information generator 206 generates the morphological information including the total value of the areas of the geographic atrophy regions, the total value of the outer perimeters of the geographic atrophy regions, and the number of the specified geographic atrophy regions. The controller 110 stores the morphological information generated in step S7 along with the above region specific information in association with the subject or the subject's eye and the inspection date in the storage unit 112.

The controller 110 according to some embodiments controls the layer thickness distribution information generator 207 to generate the two-dimensional distribution information of the layer thickness of each layer in the fundus. The controller 110 stores the distribution information generated in step S7 along with the above region specific information in association with the subject or the subject's eye and the inspection date in the storage unit 112.

S8: Display

Next, the controller 110 controls the registration processor 210 to perform registration between the front image of the fundus formed by the image forming unit 120 in advance and the image representing the geographic atrophy region specified in step S6. The display controller 111A causes the display apparatus 190 to display the image representing the geographic atrophy region superimposed on the front image of the fundus. Here, the front image of the fundus may be a shadowgram ranging from RPE to the Bruch membrane. Further, the display controller 111A causes the display apparatus 190 to display the morphological information generated in step S7 in association with the geographic atrophy region corresponding to the morphological information.

In the same manner, the controller 110 controls the registration processor 210 to perform registration between the tomographic image formed by the image forming unit 120 in advance and the image representing the geographic atrophy region specified in step S6. The display controller 111A causes the display apparatus 190 to display the image representing the geographic atrophy region superimposed on the tomographic image of the fundus. Further, the display controller 111A causes the display apparatus 190 to display the morphological information generated in step S7 in association with the geographic atrophy region corresponding to the morphological information. This terminates the operation of the ophthalmologic information processing apparatus 100 (END).

S9: Perform Trend Analysis?

When it is not determined that the analysis of the geographic atrophy region is to be performed in step S5 (S5: N), the controller 110 determines whether or not to perform trend analysis on the image of the subject's eye displayed in step S4. The controller 110 can determine whether or not to perform trend analysis based on the operation instruction signal corresponding to the operation content on the operating apparatus 180.

When it is determined that the trend analysis is to be performed (S9: Y), the operation of the ophthalmologic information processing apparatus 100 proceeds to step S10. When it is determined that the trend analysis is not to be performed (S9: N), the ophthalmologic information processing apparatus 100 terminates the operation (END).

S10: Perform Trend Analysis Processing

When it is determined that the trend analysis is to be performed in step S9 (S9: Y), the controller 110 controls the analyzer 200 to perform trend analysis processing. In step S10, in case that a predetermined analysis processing result of the data of the subject's eye is not obtained, the specification of the geographic atrophy region in step S6 and the morphology analysis in step S7 may be performed as necessary. For example, the analyzer 200 generates a trend graph of the area of the geographic atrophy region or a trend graph of the outer perimeter of the geographic atrophy region.

S11: Display in Time Series

The display controller 111A causes the display apparatus 190 to display, in time series, a plurality of atrophy region images. In each of the plurality of atrophy region images, the image representing the geographic atrophy region is overlaid on the fundus image or the tomographic image. Further, the display controller 111A causes the display apparatus 190 to display, in time series, a plurality of two-dimensional distribution information of the layer thickness in the fundus plane generated by the layer thickness distribution information generator 207 in a predetermined display region.

S12: Display Trend Graph

The display controller 111A causes the display apparatus 190 to display the trend graph, which is generated in step S10, in the predetermined display region. This terminates the operation of the ophthalmologic information processing apparatus 100 (END).

Next, an example of the operation of step S6 in FIG. 5 will be described while referring to FIGS. 6A to 13.

Figure 6A:
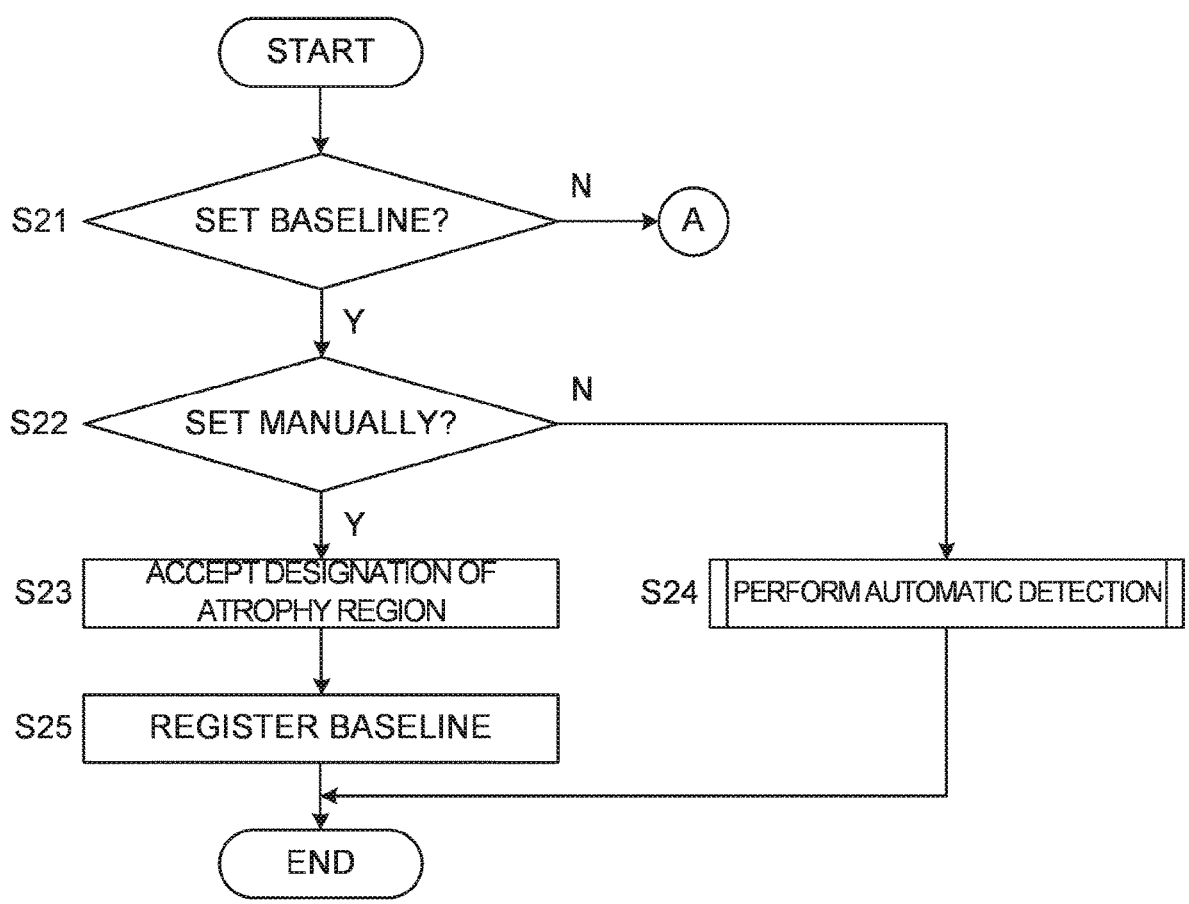
FIG. 6A is a schematic diagram illustrating an example of the operation flow of the ophthalmologic information processing apparatus according to the embodiments.
Figure 6B:
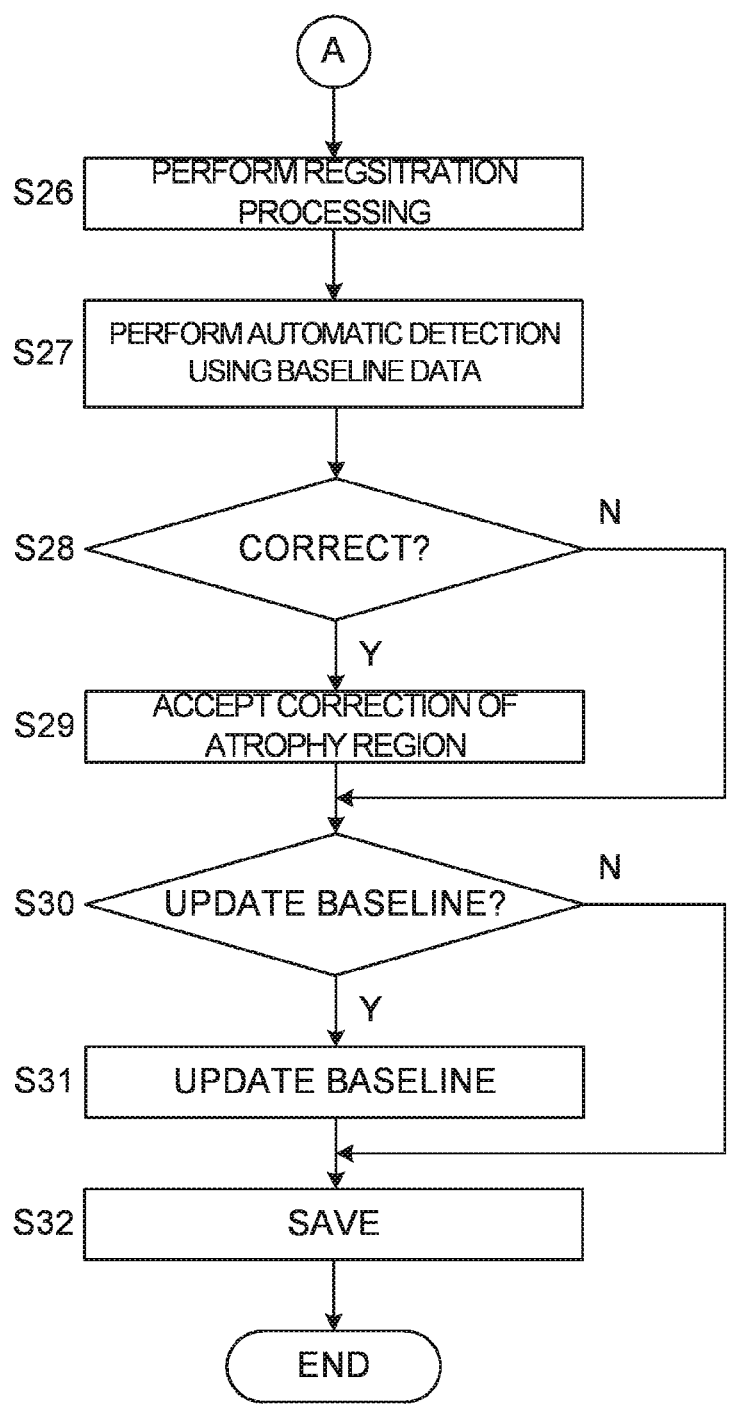
FIG. 6B is a schematic diagram illustrating an example of the operation flow of the ophthalmologic information processing apparatus according to the embodiments.

FIGS. 6A and 6B illustrate flows of an example of the operation of step S6 in FIG. 5. Besides, flows show in FIGS. 6A and 6B may be executed each time OCT data is acquired, or may be executed on each of a plurality of OCT data already acquired.

S21: Set Baseline?

In step S6 of FIG. 5, first, the controller 110 determines whether or not to set the baseline. The controller 110 can determine whether or not to set the baseline by determining whether or not the baseline is already registered based on the inspection data of the subject's eye stored in storage unit 112. In general, in case of first OCT imaging, the baseline has not been registered. Therefore, the controller 110 determines to be set the baseline. Alternatively, the controller 110 can determine whether or not to set the baseline based on the operation instruction signal corresponding to the operation content on the operating apparatus 180.

When it is determined that the baseline is to be set (S21: Y), the operation of the ophthalmologic information processing apparatus 100 proceeds to step S22. When it is determined that the baseline is not to be set (S21: N), the operation of the ophthalmologic information processing apparatus 100 proceeds to step S26.

S22: Set Manually?

When it is determined that the baseline is to be set in step S21 (S21: Y), the controller 110 determines whether or not to set the geographic atrophy region manually using the operating apparatus 180. The controller 110 can determine whether or not to be set the geographic atrophy region manually based on the operation instruction signal corresponding to the operation content on the operating apparatus 180.

When it is determined that the geographic atrophy region is to be set manually (S22 Y), the operation of the ophthalmologic information processing apparatus 100 proceeds to step S23. When it is determined that the geographic atrophy region is not to be set manually (S22 N), the operation of the ophthalmologic information processing apparatus 100 proceeds to step S24.

S23: Accept Designation of Atrophy Region

When it is determined that the geographic atrophy region is to be set manually in step S22 (S22: Y), the controller 110 reads out the data of the fundus obtained in the first OCT imaging of the subject's eye stored in the storage unit 112. The controller 110 accepts a designation operation of the geographic atrophy region by the user using the operating apparatus 180 for the read data or the image (front image) formed based on the read data. The controller 110 specifies, as the geographic atrophy region, a region designated by the user using the operating apparatus 180.

S24: Perform Automatic Detection

When it is determined that the geographic atrophy region is not to be set manually in step S22 (S22: N), the controller 110 controls the analyzer 200 (first GA region specifying unit 204A) to perform specification processing of the geographic atrophy region as described later.

S25: Register Baseline

The controller 110 controls the baseline setting unit 205A to register, as the baseline data, the geographic atrophy region set manually in step S23 or the geographic atrophy region specified by the analyzer 200 in step S24, and to register, as the baseline, the data of the fundus. This terminates the processing of step S6 in FIG. 5 (END).

S26: Perform Registration Processing

When it is determined that the baseline is not to be set in step S21 (S21: N), the controller 110 controls the analyzer 200 to perform registration processing between the baseline data registered in step S25 and the data of the fundus stored in the storage unit 112.

S27: Perform Automatic Detection Using Baseline Data

Sequentially, the controller 110 controls the analyzer 200 (second GA region specifying unit 204B) to perform specification processing of the geographic atrophy region using the baseline data described above.

S28: Correct?

Next, the controller 110 determines whether or not to correct the geographic atrophy region specified in step S27. The controller 110 can determine whether or not to correct the geographic atrophy region based on the operation instruction signal corresponding to the operation content on the operating apparatus 180.

When it is determined that the geographic atrophy region is to be corrected (S28: Y), the operation of the ophthalmologic information processing apparatus 100 proceeds to step S29. When it is determined that the geographic atrophy region is not to be corrected (S28: N), the operation of the ophthalmologic information processing apparatus 100 proceeds to step S30.

S29: Accept Correction of Atrophy Region

When it is determined that the geographic atrophy region is to be corrected in step S28 (S28: Y), the controller 110 accepts a correction operation of the geographic atrophy region by the user using the operating apparatus 180 for the geographic atrophy region specified in step S29. The controller 110 corrects the geographic atrophy region so as to be designated by the user using operating apparatus 180.

In step S29, the controller 110 controls the morphological information generator 206 to generate the morphological information representing morphology of the corrected geographic atrophy region.

S30: Update Baseline?

When it is determined that the geographic atrophy region is not to be corrected in step S28 (S28: N), or following step S29, the controller 110 determines whether or not to update the baseline to the data of the fundus. The controller 110 determines whether or not to update the baseline by determining whether or not to satisfy the update condition defined by the baseline update condition information 112A stored in the storage unit 112 based on the morphological information generated in step S29.

When it is determined that the baseline is to be updated (S30: Y), the operation of the ophthalmologic information processing apparatus 100 proceeds to step S31. When it is determined that the baseline is not to be updated (S30: N), the operation of the ophthalmologic information processing apparatus 100 proceeds to step S32.

S31: Update Baseline

When it is determined that the baseline is to be updated in step S30 (S30: Y), the controller 110 controls the baseline update unit 205B to update the baseline to the data of the fundus.

S32: Save

When it is determined that the baseline is not to be updated in step S30 (S30: N), or following step S31, the controller 110 stores the data of the fundus such as the geographic atrophy region specified newly in the storage unit 112. This terminates the processing of step S6 in FIG. 5 (END).

Figure 8:
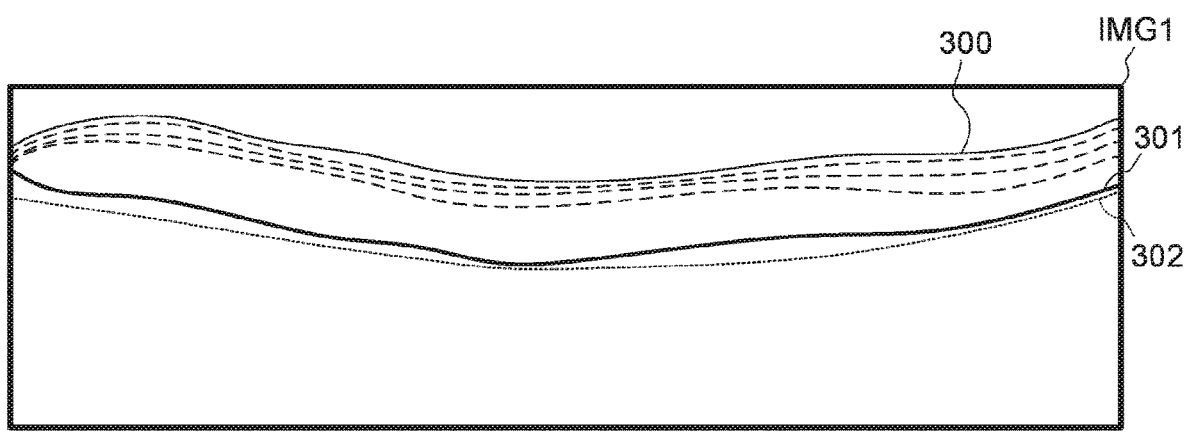
FIG. 8 is a schematic diagram for explaining an operation of the ophthalmologic information processing apparatus according to the embodiments.
Figure 9:
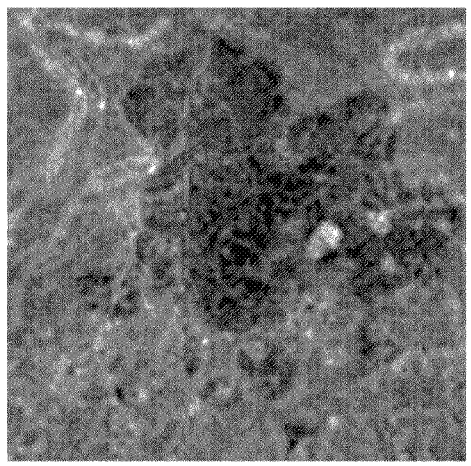
FIG. 9 is a schematic diagram for explaining an operation of the ophthalmologic information processing apparatus according to the embodiments.
Figure 10A:
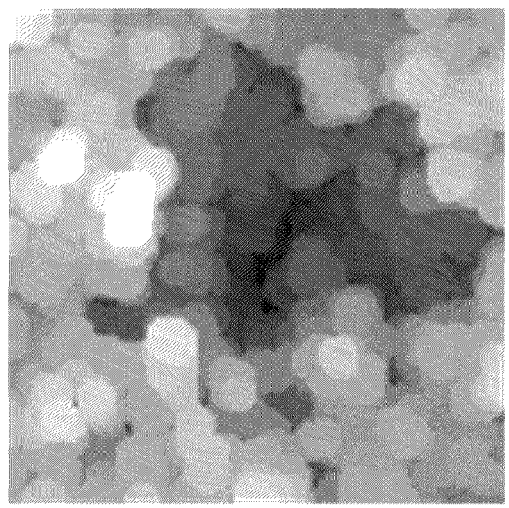
FIG. 10A is a schematic diagram for explaining an operation of the ophthalmologic information processing apparatus according to the embodiments.
Figure 10B:
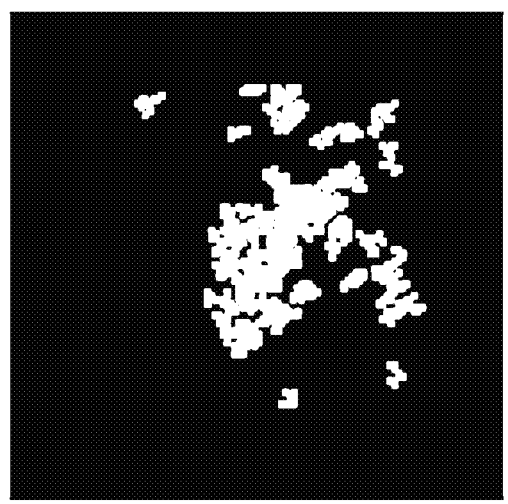
FIG. 10B is a schematic diagram for explaining an operation of the ophthalmologic information processing apparatus according to the embodiments.
Figure 11:
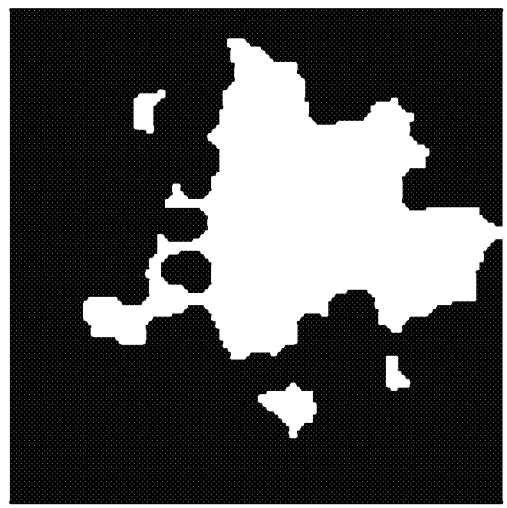
FIG. 11 is a schematic diagram for explaining an operation of the ophthalmologic information processing apparatus according to the embodiments.
Figure 12:
FIG. 12 is a schematic diagram for explaining an operation of the ophthalmologic information processing apparatus according to the embodiments.
Figure 13:
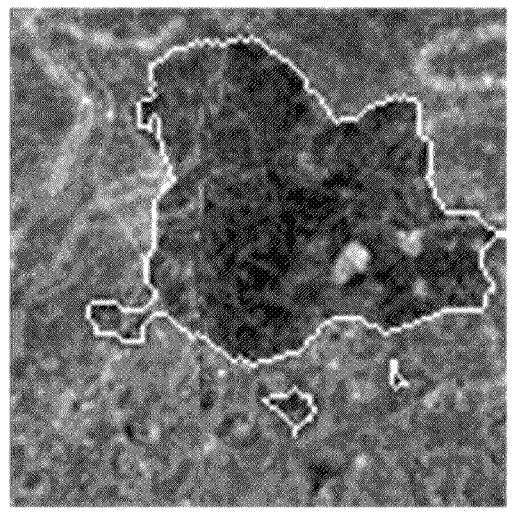
FIG. 13 is a schematic diagram for explaining an operation of the ophthalmologic information processing apparatus according to the embodiments.

FIG. 7 illustrates a flow of an example of the operation of step S24 in FIG. 6A. FIGS. 8 to 13 are operation explanatory diagrams for step S24. FIG. 8 is an operation explanatory diagram for step S42. FIG. 9 is an operation explanatory diagram for step S43. FIG. 10A is an operation explanatory diagram for step S44. FIG. 10B is an operation explanatory diagram for step S45. FIG. 11 is an operation explanatory diagram for step S46. FIGS. 12 and 13 are operation explanatory diagrams for step S47.

S41: Acquire B Scan Image

When it is determined that the geographic atrophy region is not to be set manually in step S22 as described above (S22: N), the controller 110 reads out the B scan image stored in the storage unit 112. The controller 110 may read out the data of the fundus of the subject's eye stored in the storage unit 112, and may control the image forming unit 120 to form a B scan image based on the read data. In some embodiments, in step S41, the B scan image is acquired from the ophthalmologic apparatus 10.

S42: Perform Segmentation Processing

The controller 110 controls the segmentation processor 201 to perform segmentation processing on the B scan image acquired in step S41. The segmentation processor 201 specifies a plurality of layer regions in the A scan direction for the B scan image acquired in step S41. As shown in FIG. 8, the segmentation processor 201 specifies the inner limiting membrane 300, the nerve fiber layer, the ganglion cell layer, the inner plexiform layer, the inner nuclear layer, the outer plexiform layer, the outer nuclear layer, the external limiting membrane, the photoreceptor layer, the RPE 301 which constitute the retina, in the B scan image IMG1. Further, the segmentation processor 201 specifies, as the Bruch membrane 302, a layer tissue for a predetermined number of pixels on the sclera side with respect to the specified RPE 301.

S43: Generate Contrast Map

Sequentially, the controller 110 controls the data processor 130 to generate the contrast map using the result of the segmentation processing in step S42. That is, the layer region specifying unit 202 specifies the first region and the second region by analyzing the partial data sets of the plurality of layer regions specified by the segmentation processor 201. The first region corresponds to the layer tissues on the sclera side from the region corresponding to the Bruch membrane 302. The second region corresponds to the layer tissues from the region corresponding to the inner limiting membrane 300 to the region corresponding to the RPE 301.

The distribution information generator 203 obtains, as the contrast ratio, the ratio of the integrated value of the pixel values in the A scan direction of the second region to the integrated value of the pixel values in the A scan direction of the first region, and generates the two-dimensional distribution information of the obtained contrast ratio (FIG. 9).

S44: Perform Smoothing Processing

Next, the controller 110 controls the data processor 130 to perform smoothing processing on the contrast map generated in step S43. Focusing on the fact that the change in pixel value between adjacent pixels generally tends to be small, and the noise component superimposed on the pixel value is also similar, the contrast map from which the noise component is removed by performing smoothing processing can be obtained (FIG. 10A).

S45: Perform Binarization Processing

Sequentially, the controller 110 controls the data processor 130 to perform binarization processing on the contrast map after the smoothing processing in step S44. Thereby, a binarized map as shown in FIG. 10B is obtained.

S46: Search Region

The controller 110 controls the analyzer 200 to search a region by applying a known region expansion method to the binarized map obtained in step S45 (FIG. 11).

S47: Extract Contour

The controller 110 controls the analyzer 200 to extract the contour of the region by performing known contour extraction processing on the region obtained by searching in step S46 (FIG. 12) The analyzer 200 specifies the geographic atrophy region based on the extracted contour (FIG. 13). This terminates the processing of step S24 in FIG. 6A (END).

It should be noted that the second GA region specifying unit 204B may use the contrast map shown in FIG. 10A or the binarized map shown in FIG. 10B which are obtained by the first GA region specifying unit 204A, in the specification processing of the geographic atrophy region in step S27.

Figure 14:
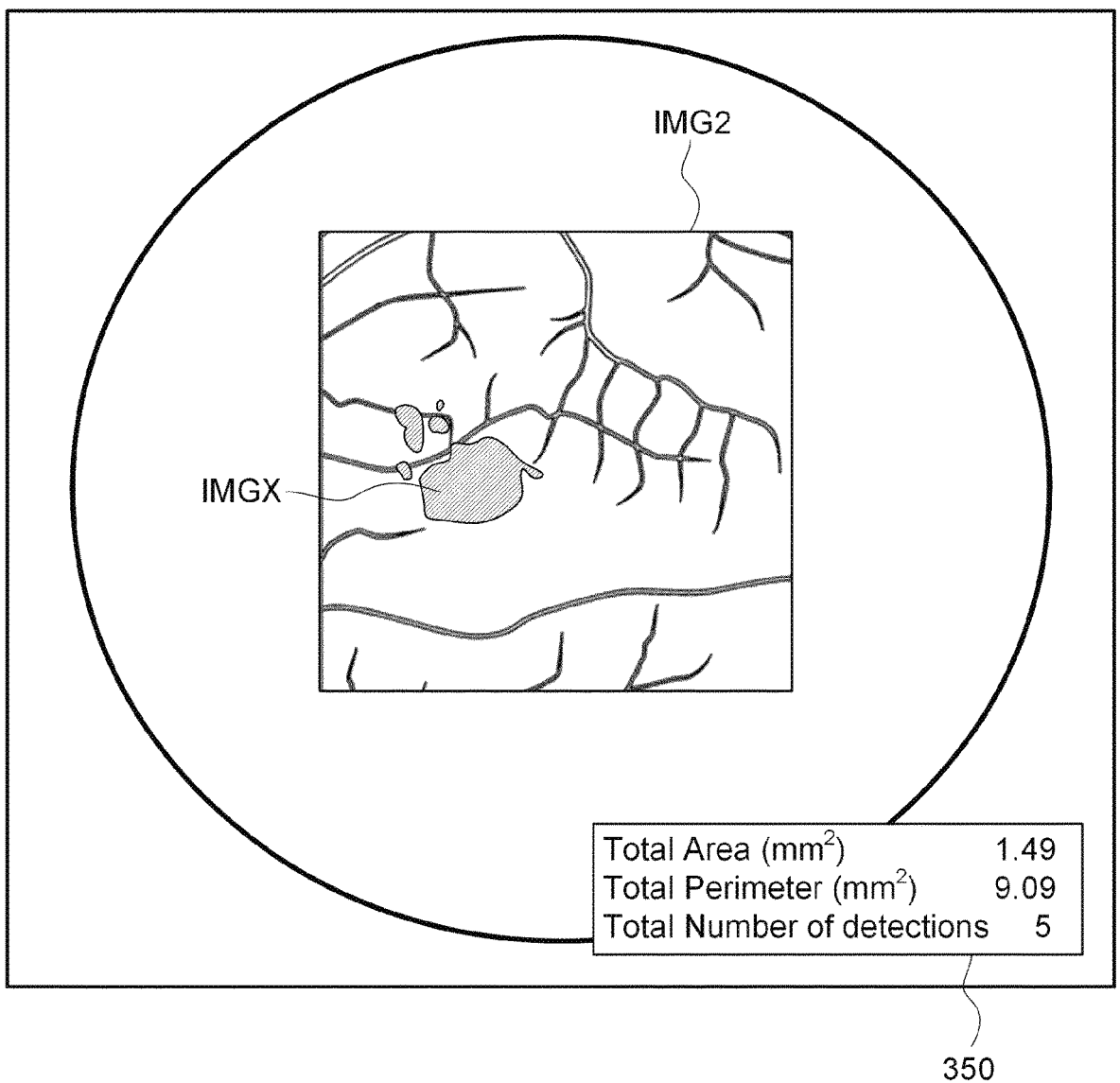
FIG. 14 is a schematic diagram for explaining an operation of the ophthalmologic information processing apparatus according to the embodiments.

FIG. 14 shows an example of the analysis information displayed on the display apparatus 190 in step S8 in some embodiments.

For example, in step S8, the display controller 111A causes the display apparatus 190 to display the image IMGX representing the geographic atrophy region superimposed on the shadowgram (the front image of the fundus) IMG2.

Further, the display controller 111A can cause the display apparatus 190 to display the morphological information 350 including the total value of the area(s) of the geographic atrophy region(s), the total value of the outer perimeter(s) of the geographic atrophy region(s), and the number of the geographic atrophy region(s). The display controller 111A according to some embodiments causes the display apparatus 190 to display the morphological information of each of the geographic atrophy region in association with the geographic atrophy region corresponding to the morphological information. Thereby, the morphology of each of the geographic atrophy region can be observed in detail.

Figure 15:
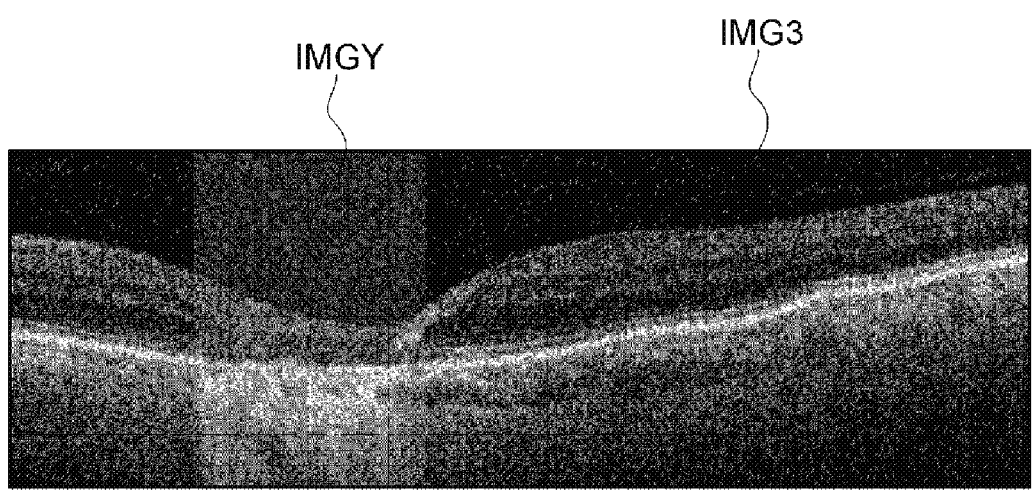
FIG. 15 is a schematic diagram for explaining an operation of the ophthalmologic information processing apparatus according to the embodiments.

FIG. 15 shows another example of the analysis information displayed on the display apparatus 190 in step S8 in some embodiments.

For example, in step S8, the display controller 111A causes the display apparatus 190 to display the image IMGY (image of B scan cross section) representing the geographic atrophy region superimposed on the B scan image IMG3 of the fundus. Thereby, the morphology of each of the geographic atrophy region can be observed in the B scan image in detail.

Figure 16:
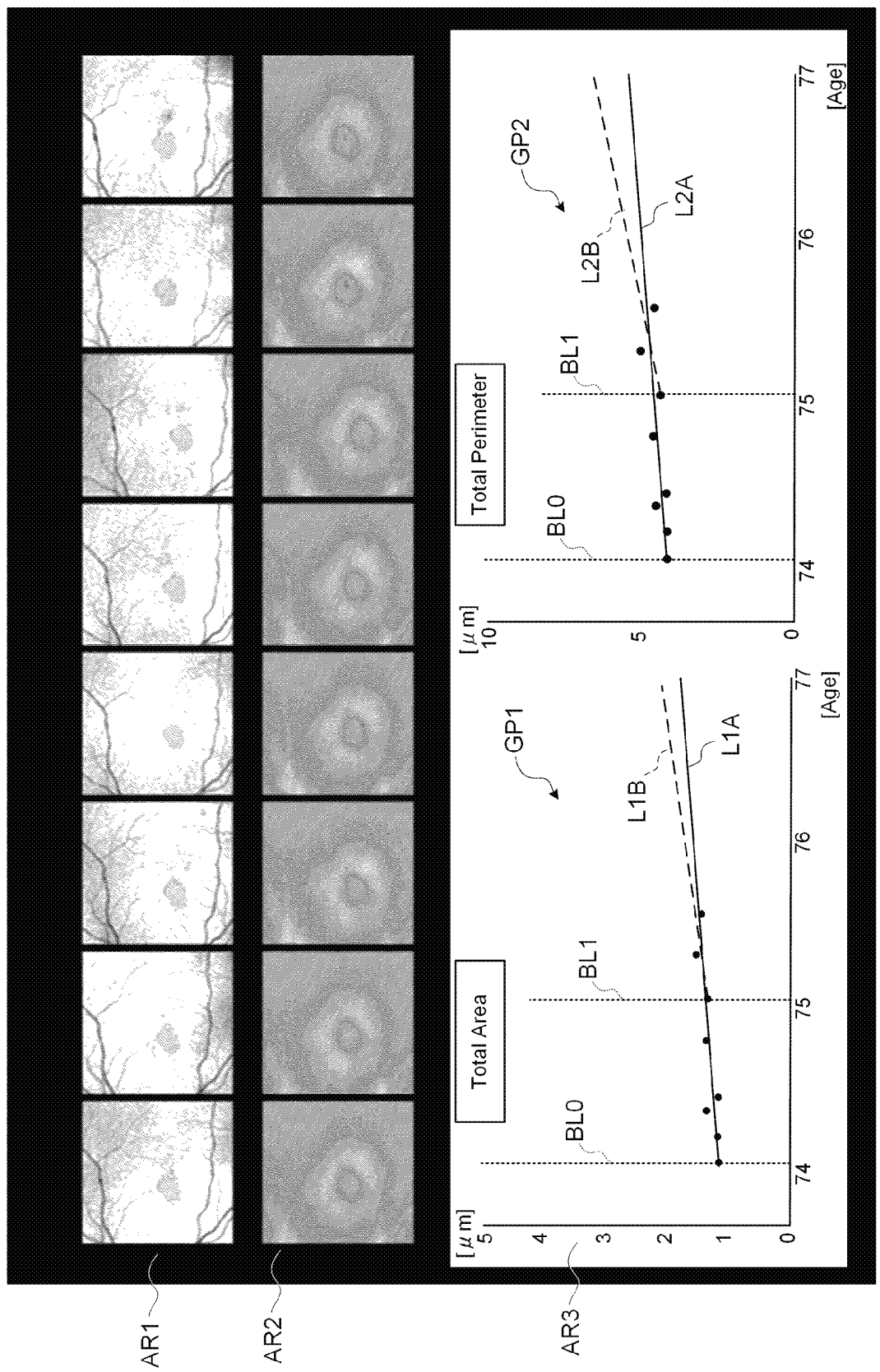
FIG. 16 is a schematic diagram for explaining an operation of the ophthalmologic information processing apparatus according to the embodiments.

FIG. 16 shows an example of the trend analysis information displayed on the display apparatus 190 in steps S11 and S12 in some embodiments.

For example, in steps S11 and S12, the display controller 111A causes the display apparatus 190 to display, in time series, a plurality of atrophy region images in a first time-series image display region AR1. In each of the plurality of atrophy region images, the image representing the geographic atrophy region specified as described above is overlaid on the fundus image (or the tomographic image). Further, the display controller 111A causes the display apparatus 190 to display, in time series, a plurality of layer thickness maps (two-dimensional distribution information of the layer thickness) in the fundus plane, which are generated by the layer thickness distribution information generator 207, in a second time-series image display region AR2. In some embodiments, the layer thickness map displayed in the second time-series image display region AR2 is displayed to correspond to the atrophy region image displayed in the first time-series image display region AR1. For example, the layer thickness map and the atrophy region image on the same inspection date displayed so as to be vertically aligned.

Further, the display controller 111A causes the display apparatus 190 to display a trend graph GP1 and a trend graph GP2 in an analysis result display region AR3. The trend graph GP1 represents the temporal change of the total value of the areas of the specified geographic atrophy regions. The trend graph GP2 represents the temporal change of the total value of the outer perimeters of the specified geographic atrophy regions.

In the trend graph GP1, the horizontal axis represents time (for example, the age of the subject), and the vertical axis represents the total value of the areas of all the specified geographic atrophy regions. In the trend graph GP1, regression straight lines L1A and L1B of the total value are displayed. The regression straight line L1A is a regression straight line of the total value on the basis of the baseline BL0. The regression straight line L1A represents the temporal change of the total value of the areas of the geographic atrophy regions on the basis of the baseline BL0. The regression straight line L1B is a regression straight line of the total value on the basis of the baseline BL1. The regression straight line L1B represents the temporal change of the total value of the areas of the geographic atrophy regions on the basis of the baseline BL1. The regression straight line L1A and the time series data of the total value of the areas after the baseline BL0 are an example of the time series information (first time series information). The regression straight line L1B and the time series data of the total value of the areas after the baseline BL1 are an example of the time series information (second time series information).

In some embodiments, the predicted value of the total value at a desired time is displayed in the trend graph GP1. In some embodiments, the scale of the horizontal axis of the trend graph GP1 or the display start timing (the first inspection date on which a trend is displayed) of the trend graph GP1 is designated by the user using the operating apparatus 180. In some embodiments, when a plot value on the trend graph GP1 is designated using the operating apparatus 180, the atrophy region image or the layer thickness map corresponding to the designated plot value is highlighted. In some embodiments, when a plot value on the trend graph GP2 is designated using the operating apparatus 180, a plotted position on the trend graph GP1 corresponding to the designated plot value is highlighted.

In the trend graph GP2, the horizontal axis represents time (for example, the age of the subject), and the vertical axis represents the total value of the outer perimeters of all the specified geographic atrophy regions. In the trend graph GP2, regression straight lines L2A and L2B of the total value are displayed. The regression straight line L2A is a regression straight line of the total value on the basis of the baseline BL0. The regression straight line L2A represents the temporal change of the total value of the outer perimeters of the geographic atrophy regions on the basis of the baseline BL0. The regression straight line L2B is a regression straight line of the total value on the basis of the baseline BL1. The regression straight line L2B represents the temporal change of the total value of the outer perimeters of the geographic atrophy regions on the basis of the baseline BL1. The regression straight line L2A and the time series data of the total value of the outer perimeters after the baseline BL0 are an example of the time series information. The regression straight line L2B and the time series data of the total value of the outer perimeters after the baseline BL1 are an example of the time series information.

In some embodiments, the predicted value of the total value at a desired time is displayed in the trend graph GP2. In some embodiments, the scale of the horizontal axis of the trend graph GP2 or the display start timing (the first inspection date on which a trend is displayed) of the trend graph GP2 is designated by the user using the operating apparatus 180. In some embodiments, when a plot value on the trend graph GP2 is designated using the operating apparatus 180, the atrophy region image or the layer thickness map corresponding to the designated plot value is highlighted. In some embodiments, when a plot value on the trend graph GP1 is designated using the operating apparatus 180, a plotted position on the trend graph GP2 corresponding to the designated plot value is highlighted.

In some embodiments, the changed contents of the display conditions (scale of horizontal axis, display start date) for the trend graph GP1 are reflected in the display conditions for the trend graph GP2 so as to be always displayed under the same display conditions.

The analyzer 200 specifies the geographic atrophy region (designated atrophy region) designated by the user using the operating apparatus 180. The display controller 111A causes the display apparatus 190 to display the specified geographic atrophy region in an identifiable manner in at least one of a plurality of atrophy region images displayed in time series.

The display controller 111A according to some embodiments causes the display apparatus 190 to display the image (trend graph etc.) representing the temporal change of the morphological information in the geographic atrophy region designated by the user using the operating apparatus 180.

Modification Example

The configuration according to some embodiments is not limited to the above configuration.

First Modification Example

The controller 110 can cause the display apparatus 190 to display display information (text information, image information) according to the difference between the geographic atrophy region which is set as the baseline data (geographic atrophy region specified by the first GA region specifying unit 204A) and the new geographic atrophy region specified by the second GA region specifying unit 204B.

Examples of the display information include information indicating that the size of the new geographic atrophy region specified by the second GA region specifying unit 204B is smaller than the geographic atrophy region set as the baseline data, information indicating that the size of the geographic atrophy region set as the baseline data and the size of the new geographic atrophy region specified by the second GA region specifying unit 204B are the same, information indicating that the size of the new geographic atrophy region specified by the second GA region specifying unit 204B is larger than the geographic atrophy region set as the baseline data, information for identifying the difference between both sided, and the like.

In case that the size of the new geographic atrophy region is smaller than the baseline data, the user can be prompted to correct the geographic atrophy region using the operating apparatus 180. In case that the size of the baseline data and the size of the new geographic atrophy region are the same, the examiner or the subject can be made to recognize that it can be judged that the progression of atrophic AMD is not observed. In case that the size of the new geographic atrophy region is larger than the baseline data, the examiner or the subject can be made to recognize that the atrophic AMD may be progressing.

Second Modification Example

The ophthalmologic apparatus according to some embodiments has at least one of the function of the ophthalmologic information processing apparatus 100, the function of the operating apparatus 180, or the function of the display apparatus 190, in addition to the function of the ophthalmologic apparatus 10.

In the following, the ophthalmologic apparatus according to a modification example of some embodiments will be described focusing on differences from the ophthalmologic apparatus according to the above embodiments.

Figure 17:
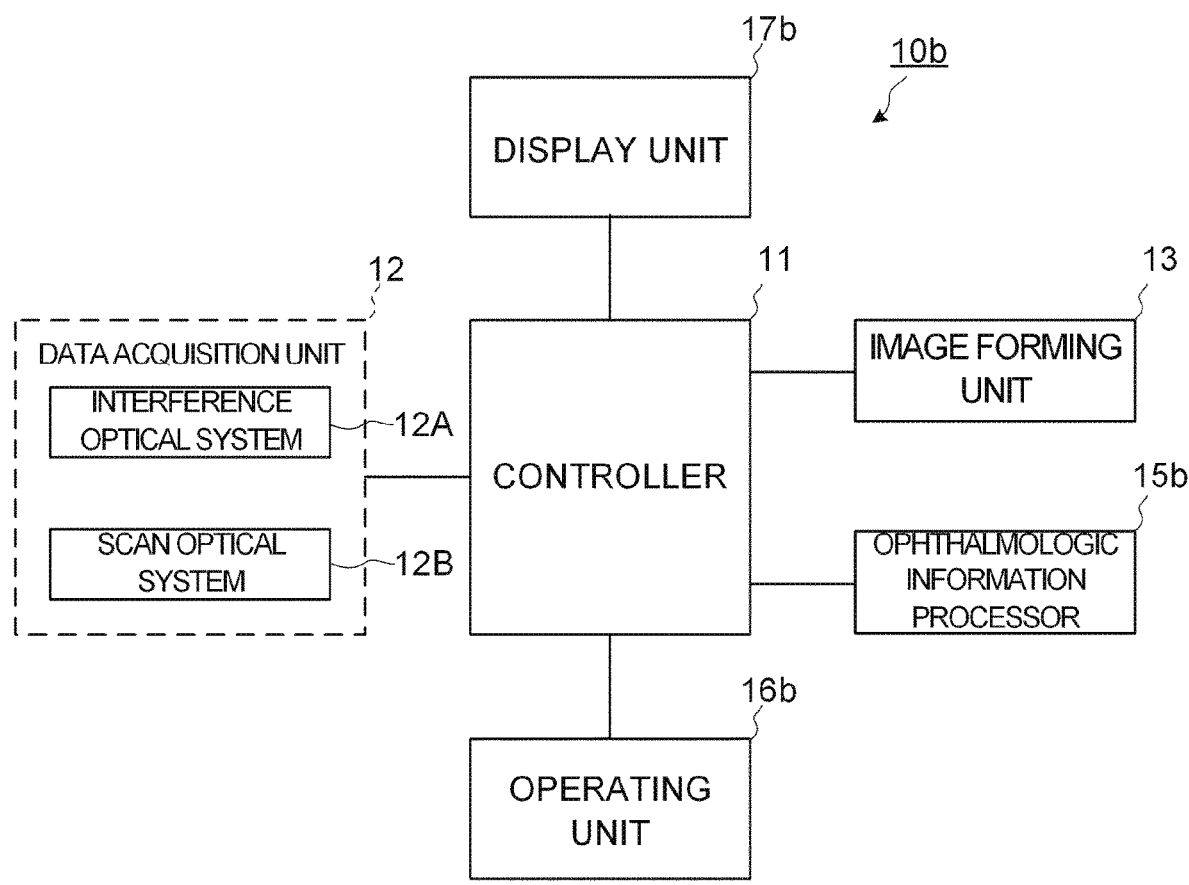
FIG. 17 is a schematic diagram illustrating an example of the configuration of the ophthalmologic apparatus according to a modification example of the embodiments.

FIG. 17 shows a block diagram of an example of the configuration of the ophthalmologic apparatus 10b according to the modification example of the embodiments. In FIG. 17, components similar to those in FIG. 2 are given the same reference numerals. The description of such components is basically omitted.

The difference between the configuration of the ophthalmologic apparatus 10b according to the present modification example and the configuration of ophthalmologic apparatus 10 according to the above embodiments is that the ophthalmologic apparatus 10b has the function of the ophthalmologic information processing apparatus 100, the function of the operating apparatus 180, and the function of the display apparatus 190. The ophthalmologic apparatus 10b includes a controller 11b, the data acquisition unit 12, the image forming unit 13, an ophthalmologic information processor 15b, an operating unit 16b, and a display unit 17b.

The controller 11b controls each part of the ophthalmologic apparatus 10b. In particular, the controller 11b controls the data acquisition unit 12, the image forming unit 13, the ophthalmologic information processor 15b, the operating unit 16b, and the display unit 17b.

The ophthalmologic information processor 15b has the same configuration as the ophthalmologic information processing apparatus 100, and has the same function as the ophthalmologic information processing apparatus 100. The operating unit 16b has the same configuration as the operating apparatus 180, and has the same function as the operating apparatus 180. The display unit 17b has the same configuration as the display apparatus 190, and has the same function as the display apparatus 190.

According to the present modification example, an ophthalmologic apparatus capable of observing in detail the morphology and the distribution of the geographic atrophy region in a compact configuration can be provided.

Effects

Hereinafter, the effects of the ophthalmologic information processing apparatus, the ophthalmologic system, the ophthalmologic information processing method, and the program according to some embodiments will be described.

An ophthalmologic apparatus (100) according to some embodiments includes a reference data setting unit (baseline setting unit 205A), a first region specifying unit (first GA region specifying unit 204A), and a second region specifying unit (second GA region specifying unit 204B). The reference data setting unit is configured to set, as first reference data, first fundus data among a plurality of fundus data of a fundus of a subject's eye acquired at different acquisition timings using optical coherence tomography. The first region specifying unit is configured to specify one or more first atrophy regions in the fundus by analyzing the first reference data. The second region specifying unit is configured to specify one or more second atrophy regions by analyzing second fundus data based on the one or more first atrophy regions, the second fundus data being acquired after the acquisition timing of the first reference data among the plurality of fundus data.

According to such a configuration, the second atrophy region can be specified by analyzing the fundus data acquired after the first reference data, based on the first atrophy region(s) specified from the fundus data set as the first reference data. Thereby, in the case where there is no effective treatment method and the atrophy region increases, the spread of the atrophy region can be detected with high accuracy. As a result, accurate follow-up of the morphology of the atrophy region or the distribution of the atrophy region in the fundus can be performed while reducing the burden on the user.

The ophthalmologic information processing apparatus according to some embodiments include a reference data update unit (baseline update unit 205B) configured to update, as second reference data, reference data using fundus data acquired after the acquisition timing of the first reference data among the plurality of fundus data, based on the one or more first atrophy regions and the one or more second atrophy regions.

According to such a configuration, the reference data can be reset appropriately according to the degree of disease progression. Thereby, the follow-up can be accurately performed on the basis of the reference data according to the progress of the disease.

In the ophthalmologic information processing apparatus according to some embodiments, the second region specifying unit is configured to specify one or more atrophy regions by analyzing second fundus data based on the one or more first atrophy regions, the second fundus data being acquired after the acquisition timing of the first reference data among the plurality of fundus data.

According to such a configuration, on the basis of the atrophy region specified in the fundus data set as the updated reference data, an atrophy region can be specified newly by analyzing the fundus data acquired thereafter. Thereby, the follow-up can be accurately performed on the basis of the reference data according to the progress of the disease.

In the ophthalmologic information processing apparatus according to some embodiments, the reference data update unit updates the first reference data to second reference data based on at least one of the number of the one or more first atrophy regions, an area of the one or more first atrophy regions, or a perimeter of the one or more first atrophy regions.

According to such a configuration, the reference data is updated based on the morphological information such as the number, the area, and the outer perimeter of the first atrophy region. Thereby, the follow-up can be accurately performed on the basis of the reference data according to the progress of the disease.

In the ophthalmologic information processing apparatus according to some embodiments, the area of the one or more first atrophy regions is an area of the first atrophy region of a part of two or more first atrophy regions.

According to such a configuration, the reference data can be updated focusing on the area of a predetermined atrophy region. Thereby, more accurate follow-up may be possible.

In the ophthalmologic information processing apparatus according to some embodiments, the perimeter of the one or more first atrophy regions is a perimeter of the first atrophy region of a part of two or more first atrophy regions.

According to such a configuration, the reference data can be updated focusing on the perimeter of a predetermined atrophy region. Thereby, more accurate follow-up may be possible.

The ophthalmologic information processing apparatus according to some embodiments includes a morphological information generator (206) configured to generate morphological information representing morphology of atrophy region specified by the first region specifying unit or the second region specifying unit, the morphological information generator generating morphological information representing morphology of the specified atrophy region for each of the plurality of fundus data including the first reference data and the second reference data, and a display controller (111A) configured to cause a display means (display apparatus 190) to display first time-series information and second time-series information, the first time-series information being time-series information of a plurality of morphological information corresponding to the fundus data acquired after the acquisition tinting of the first reference data with reference to morphological information of the first reference data, the second time-series information being time-series information of a plurality of morphological information corresponding to the fundus data acquired after the acquisition timing of the second reference data with reference to morphological information of the second reference data.

According to such a configuration, the time-series information of the morphological information on the basis of the first reference data and the time-series information of the morphological information on the basis of the second reference data are displayed on the display means. Thereby, the follow-up can be accurately performed on the basis of the reference data according to the progress of the disease.

In the ophthalmologic information processing apparatus according to some embodiments, the reference data setting unit sets the one or more first atrophy regions based on an operation content for an operating unit (operating apparatus 180).

According to such a configuration, the first atrophy region in the first reference data can be set accurately. Thereby, the specification of the atrophy region specified by analyzing the fundus data acquired after the first reference data. Thereby, the follow-up can be accurately performed on the basis of the reference data according to the progress of the disease.

An ophthalmologic system (1) according to some embodiments includes a data acquisition unit (12) configured to acquire data of the fundus using optical coherence tomography, and the ophthalmologic information processing apparatus (100) according to any one of the above.

According to such a configuration, the ophthalmologic system capable of observing in detail the morphology and the distribution of the geographic atrophy region while reducing the burden on the user can be provided.

An ophthalmologic information processing method according to some embodiments includes a reference data setting step, a first region specifying step, and a second region specifying step. The reference data setting step sets, as first reference data, first fundus data among a plurality of fundus data of a fundus of a subject's eye acquired at different acquisition timings using optical coherence tomography. The first region specifying step specifies one or more first atrophy regions in the fundus by analyzing the first reference data. The second region specifying step specifies one or more second atrophy regions by analyzing second fundus data based on the one or more first atrophy regions, the second fundus data being acquired after the acquisition timing of the first reference data among the plurality of fundus data.

According to such a method, the second atrophy region can be specified by analyzing the fundus data acquired after the first reference data, based on the first atrophy region(s) specified from the fundus data set as the first reference data. Thereby, in the case where there is no effective treatment method and the atrophy region increases, the spread of atrophy region can be detected with high accuracy. As a result, accurate follow-up of the morphology of the atrophy region or the distribution of the atrophy region in the fundus can be performed while reducing the burden on the user.

The ophthalmologic information processing method according to some embodiments include a reference data update step that updates, as second reference data, reference data using fundus data acquired after the acquisition timing of the first reference data among the plurality of fundus data, based on the one or more first atrophy regions and the one or more second atrophy regions.

According to such a method, the reference data can be reset appropriately according to the degree of disease progression. Thereby, the follow-up can be accurately performed on the basis of the reference data according to the progress of the disease.

In the ophthalmologic information processing method according to some embodiments, the second region specifying step specifies one or more atrophy regions by analyzing second fundus data based on the one or more first atrophy regions, the second fundus data being acquired after the acquisition timing of the first reference data among the plurality of fundus data.

According to such a method, on the basis of the atrophy region specified in the fundus data set as the updated reference data, a atrophy region can be specified newly by analyzing the fundus data acquired thereafter. Thereby, the follow-up can be accurately performed on the basis of the reference data according to the progress of the disease.

In the ophthalmologic information processing method according to some embodiments, the reference data update step updates the first reference data to second reference data based on at least one of the number of the one or more first atrophy regions, an area of the one or more first atrophy regions, or a perimeter of the one or more first atrophy regions.

According to such a method, the reference data is updated based on the morphological information such as the number, the area, and the outer perimeter of the first atrophy region. Thereby, the follow-up can be accurately performed on the basis of the reference data according to the progress of the disease.

In the ophthalmologic information processing method according to some embodiments, the area of the one or more first atrophy regions is an area of the first atrophy region of a part of two or more first atrophy regions.

According to such a method, the reference data can be updated focusing on the area of a predetermined atrophy region. Thereby, more accurate follow-up may be possible.

In the ophthalmologic information processing method according to some embodiments, the perimeter of the one or more first atrophy regions is a perimeter of the first atrophy region of a part of two or more first atrophy regions.

According to such a method, the reference data can be updated focusing on the perimeter of a predetermined atrophy region. Thereby, more accurate follow-up may be possible.

The ophthalmologic information processing method according to some embodiments includes a morphological information generating step that generates morphological information representing morphology of atrophy region specified in the first region specifying step or the second region specifying step, the morphological information step generating morphological information representing morphology of the specified atrophy region for each of the plurality of fundus data including the first reference data and the second reference data, and a display control step that causes a display means (display apparatus 190) to display first time-series information and second time-series information, the first time-series information being time-series information of a plurality of morphological information corresponding to the fundus data acquired after the acquisition timing of the first reference data with reference to morphological information of the first reference data, the second time-series information being time-series information of a plurality of morphological information corresponding to the fundus data acquired after the acquisition timing of the second reference data with reference to morphological information of the second reference data.

According to such a method, the time-series information of the morphological information on the basis of the first reference data and the time-series information of the morphological information on the basis of the second reference data are displayed on the display means. Thereby, the follow-up can be accurately performed on the basis of the reference data according to the progress of the disease.

In the ophthalmologic information processing method according to some embodiments, the reference data setting step sets the one or more first atrophy regions based on an operation content for an operating unit (operating apparatus 180).

According to such a method, the first atrophy region in the first reference data can be set accurately. Thereby, the specification of the atrophy region specified by analyzing the fundus data acquired after the first reference data. Thereby, the follow-up can be accurately performed on the basis of the reference data according to the progress of the disease.

A program according to some embodiments causes the computer to execute each step of the ophthalmologic information processing method described in any of the above.

According to such a configuration, the program that causes the computer to perform processing for specifying the second atrophy region(s) by analyzing the fundus data acquired after the first reference data, based on the first atrophy region specified from the fundus data set as the first reference data can be provided. Thereby, in the case where there is no effective treatment method and the atrophy region increases, the spread of the atrophy region can be detected with high accuracy. As a result, accurate follow-up of the morphology of the atrophy region or the distribution of the atrophy region on the fundus can be performed while reducing the burden on the user.

A computer program for realizing the ophthalmologic information processing method according to some embodiments can be stored in any kind of computer readable recording medium (for example, non-transitory recording medium). The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like.

The computer program may be transmitted and received through a network such as the Internet, LAN, etc.

Configurations described above are merely examples for preferably implementing the present invention. One who intends to implement the present invention may arbitrarily modify (omission, replacement, addition, etc.) within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic information processing apparatus comprising:
    a reference data setting unit configured to set, as first reference data, first fundus data among a plurality of fundus data of a fundus of a subject's eye acquired at different acquisition timings using optical coherence tomography;
    a first region specifying unit configured to specify one or more first atrophy regions in the fundus by analyzing the first reference data;
    a second region specifying unit configured to specify one or more second atrophy regions by analyzing second fundus data based on the one or more first atrophy regions, the second fundus data being acquired after the acquisition timing of the first reference data among the plurality of fundus data;
    a reference data update unit configured to update, as second reference data, reference data using fundus data acquired after the acquisition timing of the first reference data among the plurality of fundus data, based on the one or more first atrophy regions and the one or more second atrophy regions;
    a morphological information generator configured to generate morphological information representing morphology of atrophy region specified by the first region specifying unit or the second region specifying unit, the morphological information generator generating morphological information representing morphology of the specified atrophy region for each of the plurality of fundus data including the first reference data and the second reference data; and
    a display controller configured to cause a display means to display first time-series information and second time-series information, the first time-series information being time-series information of a plurality of morphological information corresponding to the fundus data acquired after the acquisition timing of the first reference data with reference to morphological information of the first reference data, the second time-series information being time-series information of a plurality of morphological information corresponding to the fundus data acquired after the acquisition timing of the second reference data with reference to morphological information of the second reference data.

2. The ophthalmologic information processing apparatus of claim 1, wherein
the second region specifying unit specifies one or more atrophy regions by analyzing third fundus data based on the one or more second atrophy regions, the third fundus data being acquired after the acquisition timing of the second reference data among the plurality of fundus data.

3. The ophthalmologic information processing apparatus of claim 1, wherein
the reference data update unit updates the first reference data to second reference data based on at least one of the number of the one or more first atrophy regions, an area of the one or more first atrophy regions, or a perimeter of the one or more first atrophy regions.

4. The ophthalmologic information processing apparatus of claim 3, wherein
the area of the one or more first atrophy regions is an area of the first atrophy region of a part of two or more first atrophy regions.

5. The ophthalmologic information processing apparatus of claim 3, wherein
the perimeter of the one or more first atrophy regions is a perimeter of the first atrophy region of a part of two or more first atrophy regions.

6. The ophthalmologic information processing apparatus of claim 1, wherein
the reference data setting unit sets the one or more first atrophy regions based on an operation instruction signal from an operating device operated by a user.

7. An ophthalmologic system comprising:
a data acquisition unit configured to acquire data of the fundus using optical coherence tomography; and
the ophthalmologic information processing apparatus according to claim 1.

8. An ophthalmologic information processing method comprising:
a reference data setting step that sets, as first reference data, first fundus data among a plurality of fundus data of a fundus of a subject's eye acquired at different acquisition timings using optical coherence tomography;
a first region specifying step that specifies one or more first atrophy regions in the fundus by analyzing the first reference data;
a second region specifying step that specifies one or more second atrophy regions by analyzing second fundus data based on the one or more first atrophy regions, the second fundus data being acquired after the acquisition timing of the first reference data among the plurality of fundus data;
a reference data update step that updates, as second reference data, reference data using fundus data acquired after the acquisition timing of the first reference data among the plurality of fundus data, based on the one or more first atrophy regions and the one or more second atrophy regions;
a morphological information generating step that generates morphological information representing morphology of atrophy region specified in the first region specifying step or the second region specifying step, the morphological information generator generating morphological information representing morphology of the specified atrophy region for each of the plurality of fundus data including the first reference data and the second reference data; and
a display control step that causes a display means to display first time-series information and second time-series information, the first time-series information being time-series information of a plurality of morphological information corresponding to the fundus data acquired after the acquisition timing of the first reference data with reference to morphological information of the first reference data the second time-series information being time-series information of a plurality of morphological information corresponding to the fundus data acquired after the acquisition timing of the second reference data with reference to morphological information of the second reference data.

9. The ophthalmologic information processing method of claim 8, wherein
the second region specifying step specifies one or more atrophy regions by analyzing third fundus data based on the one or more second atrophy regions, the third fundus data being acquired after the acquisition timing of the second reference data among the plurality of fundus data.

10. The ophthalmologic information processing method of claim 8, wherein
the reference data update step updates the first reference data to second reference data based on at least one of the number of the one or more first atrophy regions, an area of the one or more first atrophy regions, or a perimeter of the one or more first atrophy regions.

11. The ophthalmologic information processing method of claim 10, wherein
the area of the one or more first atrophy regions is an area of the first atrophy region of a part of two or more first atrophy regions.

12. The ophthalmologic information processing method of claim 10, wherein
the perimeter of the one or more first atrophy regions is a perimeter of the first atrophy region of a part of two or more first atrophy regions.

13. The ophthalmologic information processing method of claim 8, wherein
the reference data setting step sets the one or more first atrophy regions based on an operation instruction signal from an operating device operated by a user.

14. A non-transitory computer readable recording medium storing a program for causing a computer to execute each step of the ophthalmologic information processing method of claim 8.

* * * * *